US006231871B1

(12) United States Patent
Coloe

(10) Patent No.: US 6,231,871 B1
(45) **Date of Patent: *May 15, 2001**

(54) LIVE IN OVO VACCINE

(75) Inventor: Peter John Coloe, East Doncaster (AU)

(73) Assignee: American Cyanamid Company, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/643,718

(22) Filed: May 6, 1996

Related U.S. Application Data

(63) Continuation of application No. 08/147,207, filed on Nov. 3, 1993, now abandoned.

(51) Int. Cl.[7] ........................ A61K 39/112; A61K 48/00; A61K 39/02; A01N 63/00

(52) U.S. Cl. .................... 424/258.1; 424/93.2; 424/93.1; 424/93.48; 424/200.1; 424/184.1; 424/826

(58) Field of Search ............................... 424/258.1, 93.2, 424/93.1, 43.48, 200.1, 184, 826

(56) References Cited

U.S. PATENT DOCUMENTS

| | | | |
|---|---|---|---|
| 2,851,006 | 9/1958 | Taylor et al. | 119/1 |
| 3,120,834 | 2/1964 | Goldhaft et al. | 119/1 |
| 3,256,856 | 6/1966 | Nicely et al. | 119/1 |
| 4,458,630 | 7/1984 | Sharma et al. | 119/1 |
| 4,735,801 | 4/1988 | Stocker | 424/92 |
| 5,206,015 | 4/1993 | Cox et al. | 424/93 C |
| 5,210,035 | 5/1993 | Stocker | 435/172.3 |
| 6,033,670 * | 3/2000 | Bublot et al. . | |
| 6,048,535 * | 4/2000 | Sharma . | |

FOREIGN PATENT DOCUMENTS

| | | |
|---|---|---|
| 0 291 173 A2 | 11/1988 | (EP) . |
| WO 85/02545 | 6/1985 | (WO) . |
| WO 91/04749 | 4/1991 | (WO) . |

OTHER PUBLICATIONS

Hassan, J. O., and Curtiss, R. III, "Control of Colonization by Virulent *Salmonella Typhimurium* by Oral Immunization of Chickens with Avirulent Δ cya Δ crp S. Typhimurium", Res. Microbiol., 141:839–850 (1990).

Cooper, Gerard L., et al., "Vaccination of Chickens with Chicken–Derivedi *Salmonella enteritidis* phage type–4 aro–A Live Oral Salmonella Vaccines", vaccine, 10 (4) :247–254 (1992).

Stocker, Bruce A.D., "Auxotrophic *Salmonella typhi* as Live Vaccine", Vaccine, 6:141–145 (1988).

Hoiseth, Susan K., et al., "Genes aroA and serC of *Salmonella typhimurium* Constitute an Operon", *Journal of Bac.,*, 163 (1) :355–361 (1985).

Alderton, M. R., et al., "Humoral Responses and Salmonellosis Protection in Chickens Given a Vitamin–Dependent Salmonella Typhimurium Mutant", *Aviana Diseases*, 35:435–442 (1991).

Griffin, Hugh G., "Attenuated *Salmonella* as Live Vaccines: Prospects for Multivalent Poultry Vaccines", *World's Poultry Science Journal*, 47(2) :129–140 (1991).

Dougan, Gordon, et al., "Construction and Characterization of Vaccine Strains of *Salmonella* Harboring Mutations in Two Different aro Genes", *The Journal of Inf. Disease*, 158(6) :1329–1335 (1988).

Cooper, Gerard L., et al., "Vaccination of Chickens with a *Salmonella enteridtidis aroA* Live Oral Salmonella Vaccine", Microbial Pathogenesis, 9:255–265 (1990).

Dougan, Gordon, et al., "Live Bacterial Vaccines and Their Application as Carriers for Foreign Antigens", *Advances in Veterinary Science and Comparitive Medicine, vol. 33, Vaccine Biotechnology*, pp. 271–300 (1989).

O'Callaghan, David, et al., "Characterization of Aromatic– and Purine–Dependent *Salmonella typhimurium*: Attenuation, Persistence, and Ability to Induce Protective Immunity in BALB/c Mice", *Infection and Immunity*, 56(2) : 419–423 (1988).

O'Gaora, Peadar, et al., "Cloning and Characterisation of the *serC and aroA* Genes of *Yersinia enterocolitica*, and Construction of an *aroA* Mutant", *Gene*, 84:23–30 (1989).

Roberts, Mark, et al., "Construction and Characterization In Vivo of *Bordetella pertussis aroA* Mutants", *Infec. and Immunity* 58(3) :732–739 (1990).

Bowe, Frances, et al., "Virulence, Persistence, and Immunogenicity of *Yersinia enterocolitica* O:8 *aroA* Mutants", Infection and Immunity, 57(10) :3234–3236 (1989).

Dougan, Gordon, et al., "The Genetics of Salmonella and Vaccine Development", In *Biology of Salmonella*, F. Cabello, et al., eds. (Plenium Press), pp. 323–332 (1993).

Schödel, florian, et al., "Construction of a Plasmid for Expression of Foreign Epitopes as Fusion Proteins with Subunit B of *Escherichia coli* Heat–Labile Enterotoxin", *Infection and Immunity*, 57(4) :1347–1350 (1989).

Kelly, Sandra M., et al., "Characterization and Protective Properties of Attenuated Mutants of *Salmonella choleraesuis*", *Infection and Immunity*, 60:4881–4890 (1992).

* cited by examiner

*Primary Examiner*—Nita Minnifield

(74) *Attorney, Agent, or Firm*—Barbara L. Renda; Anne M. Rosenblum

(57) ABSTRACT

The present invention relates generally to modified microorganisms suitable for use as live in ovo vaccines for avian species. The live in ovo vaccines of the present invention are useful for inducing immunity before or immediately after hatching against a virulent form of the modified microorganism or a microorganism immunologically related to the modified microorganism or a virulent organism or virus carrying an antigenic determinant expressed by the modified microorganism in the live vaccine. The subject live in ovo vaccines are particularly efficacious in enhancing the survival rate of newly-hatched poultry birds.

26 Claims, 10 Drawing Sheets

LIVE IN OVO VACCINE

RELATED APPLICATIONS

This application is a continuation of U.S. application Ser. No. 08/147,207, filed Nov. 3, 1993 (now abandoned).

FIELD OF THE INVENTION

The present invention relates generally to modified microorganisms suitable for use as live in ovo vaccines for avian species. The live in ovo vaccines of the present invention are useful for inducing immunity before or immediately after hatching against a virulent form of the modified microorganism or a microorganism immunologically related to the modified microorganism or a virulent organism or virus carrying an antigenic determinant expressed by the modified microorganism in the live vaccine. The subject live in ovo vaccines are particularly efficacious in enhancing the survival rate of newly-hatched poultry birds.

BACKGROUND OF THE INVENTION

Infection of avian species by microorganisms, viruses, helminths, yeasts and protozoans can have serious environmental, ecological and commercial implications. Not only are the birds themselves at risk, but there is also the potential of the infecting agent to spread to other animals, including humans.

The poultry industry is particularly vulnerable to significant economic losses due to the susceptibility of stock birds, and in particular newly-hatched stock birds, to rapidly spreading infections. In poultry birds, infection by Salmonella species, generally referred to as salmonellosis, is the most common form of infection causing high mortality rates. Many species of Salmonella also cause infection in humans and other animals and, hence, control of salmonellosis in poultry birds is of particular importance. Two of the most common species of Salmonella isolated from poultry birds are *Salmonella typhimurium* and *Salmonella enteritidis*. Both organisms contribute significantly to the outbreaks of salmonellosis and, in fact, *S. enteritidis* phage type 4 emerged as a significant threat to public health in Britain during the mid 1980's.

Chemotherapy and chemoprophylaxis have been used as forms of protective measures to combat poultry diseases such as salmonellosis. However, such measures are not always successful, are quite expensive, may lead to the development of drug resistance amongst infecting agents and are not necessarily acceptable to public health authorities for birds destined for human or animal consumption. For these and other related reasons, alternative forms of protection for avian species have been the subject of intense scientific research.

One form of protection proposed is the development of vaccines against poultry diseases. Live attenuated Salmonella vaccines have been shown to protect chickens (Cooper et al., *Microb. Pathog.,* 9: 255–265, 1990; Hassan and Curtiss III, *Res. Microbiol.,* 141: 839–850, 1990). Furthermore, Salmonella strains with a transposon inserted at or near aroA of the aromatic biosynthetic pathway have been shown to be attenuated, yet still capable of residing in tissue for sufficient time to stimulate an immune response (Stocker, *Vaccine,* 6: 141–145, 1988; U.S. Pat. No. 4,735,801; U.S. Pat. No. 5,210,035). Cooper, et al., *Vaccine* 10: 247–254, 1992, made two strains of *S. enteritidis* phage type 4 with mutations in the aroA gene. These mutant strains were used as a live oral vaccine against oral and intravenous challenge. The results presented by Cooper et al., supra, showed that the *S. enteritidis* vaccines were protective in chickens following oral ingestion.

Notwithstanding the purported efficacy of the live oral vaccines comprising Salmonella species in protecting chickens, newly-hatched birds are particularly susceptible to Salmonella infection and a high mortality rate immediately post-hatching can have serious economic consequences. Furthermore, administering live oral vaccines is not always convenient and difficulties may result in ensuring adequate doses are received by the birds. Another option, therefore, is to inoculate the birds when in ovo.

European Patent Application No 0 291 173 proposed the administration of a non-replicating immunogen designed to induce immunity in embryos prior to hatching. The method was said to be especially useful for immunizing birds against avian coccidiosis using a sporulated *Eimeria tenella* oocyst extract. U.S. Pat. No. 4,458,630 also teaches that birds can be immunized against Marek's disease by injecting eggs, prior to hatching, with a replicating viral vaccine. However, in both cases, inoculation was intra-embryo, such as into the yolk sac or chorion allantoic fluid. If bacteria were to be inoculated in such a manner, the bacteria would "blow" the egg, causing it to go rotten and causing the embryo to die.

There is a need, therefore, to improve the technology relating to in ovo vaccines so that avian species can be protected against challenge by virulent organisms such as virulent strains of Salmonella. In accordance with the present invention, the inventors have discovered that microorganisms rendered attenuated or avirulent may be inoculated into defined tissues in ovo and that birds upon hatching are protected from challenge with a corresponding wild-type microorganism. The method of the present invention also enables the use of the modified microorganisms to carry antigenic epitopes in the form of immunogens for other avian pathogens to induce immunity against those pathogens. The present invention represents a major breakthrough in protecting newly-hatched birds and offers significant commercial advantages to poultry management.

SUMMARY OF THE INVENTION

Accordingly, one aspect of the present invention provides a live in ovo vaccine for avian species comprising an attenuated microorganism which:

(a) exhibits auxotrophy to one or more growth factors, such that it is incapable of growing on a minimal medium in the absence of said one or more growth factors;

(b) is capable of colonizing one or more tissues in an embryo prior to hatching; and (c) is capable of inducing before or immediately after hatching an immune response in the embryo against a virulent form of said microorganism or an immunologically cross-reactive microorganism or a virulent organism or virus carrying an antigenic determinant expressed by said attenuated microorganism.

Another aspect of the present invention contemplates a live in ovo vaccine for poultry birds comprising an attenuated Salmonella which:

(a) exhibits auxotrophy for one or more growth factors such that it is incapable of growing on a minimal medium in the absence of said one or more growth factors;

(b) is capable of colonizing one or more tissues in an embryo prior to hatching; and (c) is capable of inducing before or immediately after hatching an immune response in the embryo against a virulent form of said Salmonella or an immunologically cross-reactive Salmonella or a virulent organism or virus carrying an antigenic determinant expressed by said avirulent Salmonella.

Yet another aspect of the present invention is directed to a method for immunizing an avian species against infection by a pathogenic microorganism said method comprising administering in ovo an attenuated microorganism which:

(a) exhibits auxotrophy to one or more growth factors such that it is incapable of growing on a minimal medium in the absence of said one or more growth factors; and (b) is capable of colonizing one or more tissues in an embryo prior to hatching in an amount and under conditions effective to induce an immune response in the embryo before or immediately after hatching against a virulent form of said attenuated microorganism or an immunologically cross-reactive microorganism or virulent organism or virus carrying an antigenic determinant expressed by said attenuated microorganism.

Still yet another aspect of the present invention relates to a method for immunizing poultry birds against infection by a pathogenic microorganism said method comprising in ovo administration of a vaccine comprising an attenuated Salmonella which:

(a) exhibits auxotrophy to one or more growth factors such that it is incapable of growing on a minimal medium in the absence of said one or more growth factors; and (b) is capable of colonizing one or more tissues in an embryo prior to hatching in an amount and under conditions effective to induce an immune response in the embryo before or immediately after hatching against a virulent form of said Salmonella or a virulent organism or virus carrying an antigenic determinant expressed by said attenuated Salmonella.

Another aspect of the present invention contemplates a fertilized egg from a poultry bird having an air sac wherein the air sac is inoculated with a modified microorganism which:

(a) exhibits auxotrophy to one or more growth factors such that it is incapable of growing on a minimal medium in the absence of said one or more growth factors; and (b) is capable of colonizing one or more tissues in an embryo prior to hatching after the embryo breaks through the air sac; and (c) is capable of inducing an immune response in the embryo before or immediately after hatching against a virulent form of said microorganism or an immunologically cross-reactive microorganism or virulent organism or virus carrying an antigenic determinant expressed by said avirulent microorganism.

DETAILED DESCRIPTION OF THE INVENTION

Figure 1:
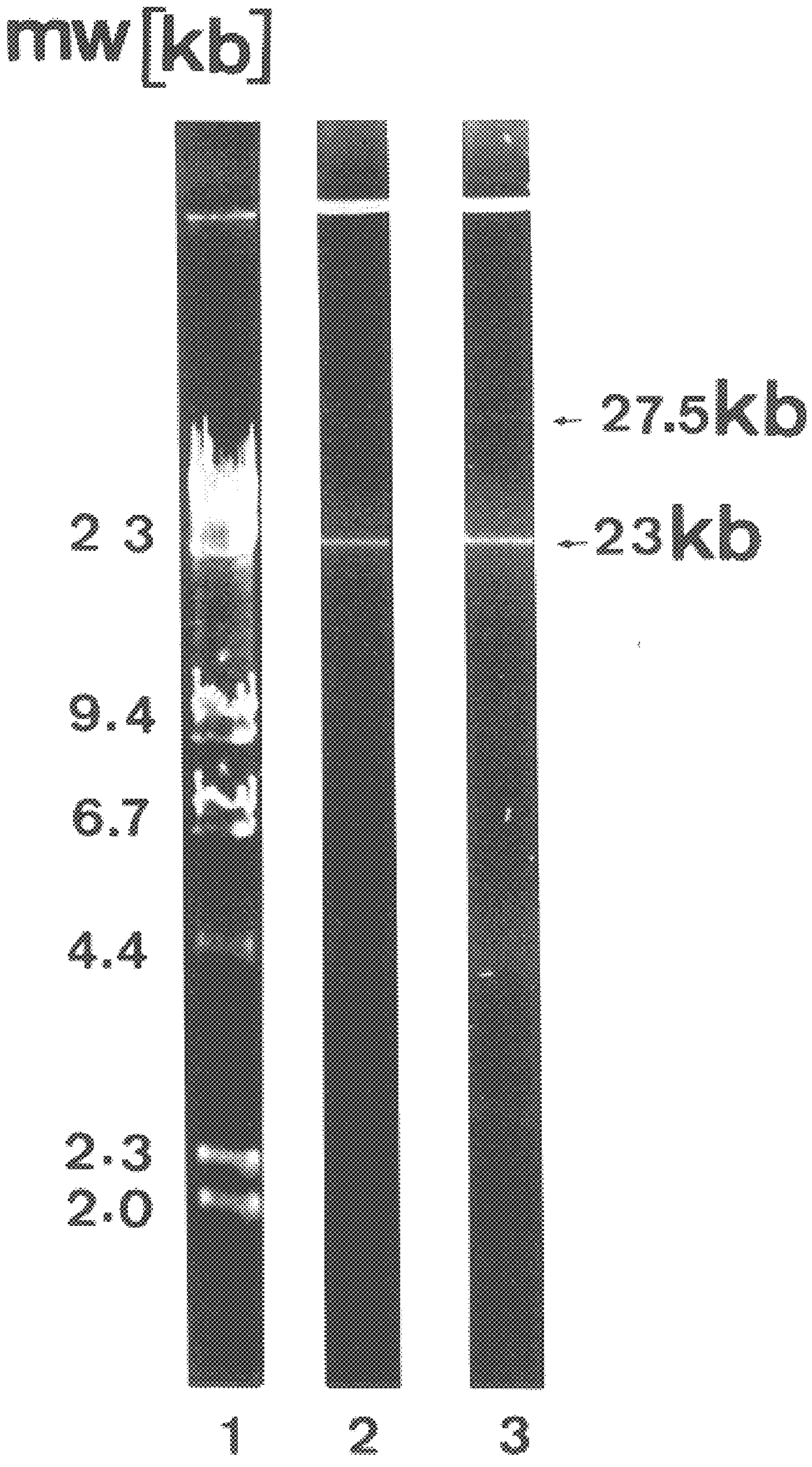
FIG. 1 is a photographic representation of the plasmid profile in *S. typhimurium* STM-1 and in its wild-type parent. Lane 1: HindIII digested Lambda standard; Lane 2: wild-type; Lane 3: STM-1.

One aspect of the present invention provides modified microorganisms in the form of live in ovo vaccines capable of facilitating protection of avian species from microbial infection or to immunize the avian species against an immunogen expressed in the live vaccine. The term "live in ovo vaccine" as used in the specification and claims herein, is to be considered in its broadest sense and specifically includes an attenuated or avirulent microorganism incapable of replicating in a minimal medium while retaining its ability to colonize embryonic tissue in ovo prior to hatching. The preferred embryonic tissue in this regard is associated with the air sac and is, in particular, the air sac membrane. After hatching or immediately prior to hatching, the attenuated or avirulent microorganism colonizes tissues such as the colon, respiratory tract and lung. The live in ovo vaccine of the present invention may also provide the additional advantage of competitively excluding pathogenic microorganisms from the newly-hatched bird, and the presence of the vaccine may generally stimulate the immune system in the birds against other potential antigens.

Avian species contemplated by the present invention include chickens, ducks, turkeys, geese, bantams, quail and pigeons. The most preferred avian species are commercially important poultry birds such as chickens, ducks and turkeys.

Candidates for use in live in ovo vaccines may be selected on the basis of the protection sought. For example, where protection is sought against a particular species of microorganism or genus of microorganism, then an attenuated or avirulent strain of the species or genus is selected. Such a selection requires that the attenuated or avirulent microorganism retain the ability to induce an immune response cross-reactive with a corresponding wild-type strain while not being pathogenic to either the avian species or other animals such as humans. However, where the live in ovo vaccine is being used as a carrier for an immunogen, and generally a recombinant immunogen, then it is not essential that the attenuated or avirulent microorganism induce a cross-reactive immune response to its corresponding wild-type microorganism. Although it may seem advantageous that the immunogen or antigenic epitope carried by the attenuated or avirulent microorganism be exposed on the cell surface or synthesized and released by the cell to an extent sufficient to induce an immune response to the immunogen or antigenic epitope, it may not be essential. Such an immune response then protects the avian species from infection by microorganisms or other pathogenic agents, naturally expressing the immunogen.

Avian pathogenic agents contemplated by this aspect of the present invention include one or more agents selected from microorganisms, helminths, protozoans, yeasts and viruses. Preferred immunogens or antigenic epitopes are those from the causative agents of avian leucosis, reticuloendoetheliosis, infectious bronchitis, infectious bursal disease, Newcastle's disease, adenovirus disease, reovirus disease, pox disease, laryngotracheitis, avian influenza, infectious coryza, fowl typhoid, coccidiosis, cryptosporidiosis and fowl cholera. Another preferred immunogen or antigenic epitope is from the species Eimeria such as from *Eimeria acervulina, Eimeria mivati, Eimeria mitis, Eimeria praecox, Eimeria hagani, Eimeria necatrix, Eimeria maxima, Eimeria brunetti* and *Eimeria tenella.* The most preferred species is *E. tenella.*

Regardless of the criteria employed to select the candidate microorganism for use in a live in ovo vaccine, the subject microorganism must be processed to render same attenuated or avirulent (where the organism is pathogenic) and/or to induce one or more mutations substantially incapable of reversion. A substantially non-revertible mutant is considered herein to have a reversion frequency of $\leqq 10^{-8}$, more preferably $\leqq 10^{-9}$ and even more preferably $\leqq 10^{-10}$. In a most preferred embodiment, the present invention contemplates a mutation with, in effect, a zero probability of reversion.

A suitable mutation involves single or more preferably multiple nucleotide substitutions, deletions and/or additions to a target genetic sequence in the genome of a candidate microorganism. In this context, a genome includes extrachromosomal elements such as plasmid DNA. The mutation is designed to ensure that the organism is incapable of growing on minimal medium due to its inability to synthesise one or more factors essential for growth of the microorganism. Such a mutant organism is known as a auxotrophic mutant. The mutation to auxotrophy may also result in attenuation or avirulance of the microorganism or the latter may require additional steps such as continual passage through nutrient media. The use of an auxotrophic mutant in the live in ovo vaccine assists in reducing spread of the organism by the bird shedding a microorganism substantially incapable of growing in the environment.

The method of the present invention is predicated in part on the use of an attenuated or avirulent microorganism capable of colonizing embryonic tissue and, in particular, air sac tissue, while being substantially non-pathogenic to the embryo. The preferred site of inoculation is tissue associated with the air sac, such as the air sac membrane, and the modified organisms of the present invention are considered those capable of colonizing the air sac side of the air sac membrane while being substantially non-pathogenic to the developing embryo, that is, cause no embryo death, or reduced embryo death compared to wild-type organisms. Such organisms, however, may show some degree of pathogenicity if inoculated into different parts of the embryonic tissue.

Preferred organisms useful for practices in the present invention are species of Salmonella, Shigella, Klebsiella, Enterobacter, Serratia, Proteus, Yersinia, Vibrio, Aeromonas, Pasteurella, Pseudomonas, Acinetobacter, Moraxella, Flavobacterium, Mycoplasma and *Escherichia coli.* Such microorganisms after being rendered attenuated or avirulent are useful for inducing immunity to wild-type strains or to antigens such as recombinant antigens expressed therein. More preferred microorganisms includes species of Salmonella such as *Salmonella typhimurium, Salmonella paratyphi* A or C, *Salmonella schottmulleri, Salmonella choleraesuis, Salmonella Montevideo, Salmonella newport, Salmonella enteritidis, Salmonella gallinarum, Salmonella pullorum, Salmonella abortusovi, Salmonella abortus-equi, Salmonella dublin, Salmonella sofia, Salmonella havana, Salmonella bovismorbificans, Salmonella hadar, Salmonella arizonae* and *Salmonella anatum,* and others which are known to infect avian species and, in particular, poultry birds. It is particularly preferred to select a species of Salmonella which expresses antigens immunologically related to one or more other Salmonella species to facilitate cross species protection.

Preferred Salmonella species are Group B, C (including $C_1$ and $C_2$) and D Salmonella based on serological testing of lipopolysaccharide antigens. Even more preferred Salmonella include *S. typhimurium* and *S. enteritidis.* The most preferred microorganism is *S. typhimurium.*

The microorganisms such as Salmonella species and in particular *S. typhimurium* are modified by inducing a mutation in a biosynthetic pathway of, for example, an amino acid or vitamin or other essential molecule. The mutation may affect biosynthesis of one or more of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and/or valine. The preferred site of the mutation is in an aromatic vitamin biosynthetic pathway and, in particular, the aro pathway. In this pathway, phosphoenolpyruvate and erythrose-4-phosphate condense to form 3-deoxyarabinoheptulosonic acid-7-phosphate. The pathway continues through a series of intermediates such as shikimate, chorismate and anthranilate to produce L-tryptophan. From chorismate is produced molecules such as p-aminobenzoate (leading to folate), p-hydroxybenzoate (leading to ubiquinones), 3,4-dihydroxybenzoate (leading to vitamin K) and prephenate (leading to L-phenylalanine and L-tyrosine). The preferred site of the mutation is in a gene before chorismate and is preferably in one or more of aroA, aroB, aroC or aroD. The most preferred site of mutation is selected to attenuated or render the organism avirulent while permitting the organism to still invade and colonize tissues. Such a mutation is one in the aroA gene.

Any number of techniques may be employed to modify the microorganism to induce the mutation in the biosynthetic pathway. One suitable technique involves the use of translocatable elements such as transposons. Transposons are segments of double stranded DNA which normally comprise a gene for resistance to an antibiotic or other selectable marker together with the required genes to effect an insertion of a transposon at one or more sites in the genome of the microorganism. The location of the transposon inserted into the genome of the subject microorganism may be determined functionally by determining the auxotrophic requirements of the organisms and/or genetically by, for example, hybridization using a suitable probe. The modified microorganism may be used with the transposon inserted into the target gene, or loss of the transposon may be selected by, for example, loss of antibiotic resistance or loss of the selectable marker. Frequently, the excision of a transposon is concomitant with excision of adjacent DNA resulting in a deletion of the target sequence. A preferred type of deletion in this regard results in the loss of two or more nucleotides, and preferably results in the loss of two to five nucleotides and more preferably results in the loss of more than five contiguous nucleotides.

The mutation of a particular microorganism can be facilitated by techniques such as transduction, conjugation and transformation. For example, a general transducing phage (for example, P1 or P22) can be used to transduce a non-functional biosynthetic gene such as when inactivated by the insertion (or excision) of a transposon from its original host to a new target microorganism. Given the broad host range of phages like P1 or P22, the potential is increased of making the same mutation in a range of organisms. Conjugation may be employed involving conjugational crossing of a virulent strain with a non-virulent strain having a desired non-reverting mutation in a biosynthetic gene. Transfer of a mutated gene may occur from Hfr or $F^+$ strain by crossing same with a $F^-$ virulent strain which would result in recombinational replacement of a wild-type gene by a mutated gene. The use of such techniques is particularly useful in inducing two or more independent mutations in two or more biosynthetic pathways. These techniques may also be employed to introduce heterologous antigens from other species or avian pathogens.

The exemplified and most preferred microorganism is *S. typhimurium* strain STM-1 for use in poultry birds. It has been surprisingly discovered that this strain of *S. typhimurium* is capable of colonizing the air sac side of the air sac membrane, while not being particularly pathogenic to the embryo following this colonization. It has also been surprisingly discovered that this strain can invade and colonize tissues in the embryo and newly-hatched birds to permit the establishment of an immune response against virulent forms of the organism or immunologically related microorganisms. The exemplification of *S. typhimurium* STM-1 is in no way intended to limit the present invention to the microorganism and the present invention extends to all modified organisms capable of being used as live in ovo vaccines as herein described.

A sample of *Salmonella typhimurium* STM-1 was deposited at the Australian Government Analytical Laboratories (a Budapest Treaty Depositry), 1 Suakin Street, Pymble, New South Wales, 2037, Australia, on Oct. 25, 1993, and has been assigned accession number N93/43266. The parent, wild-type strain was originally isolated from a flock of chickens infected with Salmonella. Phage P22 transduction was then used to transduce into *S. typhimurium* STM-1 a transposon Tn:10 insertion in the aroA gene from *S. typhimurium* LT2. Transposon delete mutants which were also $aroA^-$ were then selected. *S. typhimurium* STM-1 is also auxotrophic for serine.

According to this aspect of the present invention, there is provided a modified Salmonella microorganism suitable for use as a live in ovo vaccine. This modified Salmonella microorganism carries a substantially non-reverting mutation in a gene encoding an enzyme of a biosynthetic pathway. More particularly, the present invention provides a mutant strain of *S. typhimurium* suitable for use as a live in ovo vaccine. This mutant carries a substantially non-reverting mutation in a gene encoding an enzyme required for chorismate biosynthesis in said microorganism. Preferably, the mutation is in aroA, aroB or aroC. More preferably, the mutation is in aroA and, still more preferably, the microorganism carries one or more mutants in another biosynthetic pathway such as the biosynthetic pathway for serine. Most preferably, the organism is *S. typhimurium* STM-1.

The modified microorganisms of the present invention are used in the preparation of an in ovo vaccine. According to this aspect of the present invention, there is provided an in ovo vaccine comprising a modified Salmonella microorganism carrying a substantially non-reverting mutation in a gene encoding an enzyme of a biosynthetic pathway. More particularly, the present invention provides an in ovo vaccine comprising a mutant strain of *S. typhimurium* which carries a substantially non-reverting mutation in a gene encoding an enzyme required for chorismate biosynthesis in said microorganism. Preferably, the mutations and the microorganism are as hereinbefore defined. Even more preferably, the in ovo vaccine comprises *S. typhimurium* STM-1.

The vaccine composition of the present invention must be suitable for injectable use into the egg. The vaccine may comprise a single type of modified microorganism and may also contain two or more types depending on whether a multivalent vaccine is required. The composition must further have sufficient fluidity to permit easy syringability and should also not contain contaminating bacteria or other organisms. In this regard, one convenient approach is to use a modified microorganism which is resistant to a particular antibiotic and then to maintain the organism in the presence of the antibiotic in the vaccine composition. The presence of the antibiotic will kill or inhibit the growth of contaminating organisms.

The term "multivalent" vaccine is used in its most general sense and extends to a modified microorganism capable of stimulating an immune response directed to at least two antigenic epitopes expressed on or by the modified microorganism. In this regard, a multivalent vaccine includes, for example, a microorganism capable of inducing an antibody response to two distinct antigenic epitopes on or expressed by the modified microorganism where the two or more epitopes are indigenous to the modified microorganism. More commonly, however, a multivalent vaccine includes a modified microorganism capable of inducing an immune response to virulent forms of said microorganism as well as to heterologous antigens expressed by said microorganisms (such as recombinant antigens or those introduced by transduction, conjugation or transformation) and which are not indigenous to the microorganism. In this regard, the multivalent vaccine is directed to two or more pathogenic agents.

The preferred multivalent vaccines are those capable of inducing an immune response to one or more species of Salmonella and to at least one antigenic epitope from one or more avian pathogenic agents selected from microorganisms, helminths, protozoans, yeasts and viruses. Salmonella species contemplated by this aspect of the present invention comprise and include one or more of *Salmonella typhimurium, Salmonella paratyphi* A or C, *Salmonella schottmulleri, Salmonella choleraesuis, Salmonella montevideo, Salmonella newport, Salmonella enteritidis, Salmonella gallinarum, Salmonella pullorum, Salmonella abortusovi, Salmonella abortus-equi, Salmonella dublin, Salmonella sofia, Salmonella havana, Salmonella bovismorbificans, Salmonella hadar, Salmonella arizonae* and *Salmonella anatum.*

More preferably, the immune response is in respect of *S. typhimurium* and/or *S. enteritidis.* Avian pathogenic agents other than Salmonella species contemplated by this aspect of the present invention comprise and include the causative agent of one or more antigenic epitopes from one or more causative agents of avian leucosis, reticuloendoetheliosis, infectious bronchitis, infectious bursal disease, Newcastle disease, adenovirus disease, reovirus disease, pox disease, laryngotracheitis, avian influenza, infectious coryza, fowl typhoid, cryptosporidiosis, coccidiosis and fowl cholera.

The preferred causative agent is a species of Eimeria such as *Eimeria acervulina, Eimeria mivati, Eimeria mitis, Eimeria praecox, Eimeria hagani, Eimeria necatrix, Eimeria maxima, Eimeria brunetti* and *Eimeria tenella.* The most preferred Eimeria species is *E. tenella.*

Conveniently, the modified microorganism is maintained in freeze dried form or may be maintained in a frozen condition. Such conditions include, for example, storage in glycerol or other suitable medium at −70° C. Generally, the modified microorganism when stored comprises a minimal viable concentration of $10^6$–$10^{12}$ cells per dose of reconstituted vaccine. The stored modified microorganisms are readily reconstituted in a simple growth medium such as nutrient broth or a tryptic soy broth supplemented with a yeast extract. Tryptic soy broth contains digests of casein and soya bean meals together with dextrose, sodium chloride and dipotassium phosphate. When growing large volumes of vaccine culture, it is particularly convenient initially to grow 200–700 ml cultures and use these to inoculate 7–15 liters of growth medium. These large volume cultures are then used to inoculate a production fermenter. The growth of the culture in the fermenter is monitored by any convenient means such as by optical density. When optical density is the growth parameter, at peak density the culture biomass is retained, checked for purity and then chilled and concentrated and blended with a suitable carrier prior to freeze-drying. Where the storage technique is lyophilization, sterile nitrogen gas may be used to back fill samples containing the culture biomass. The lyophilized culture can be reconstituted in any suitable diluent and then used for immediate injection into the egg. Any suitable carrier may be used, with the most preferred carrier being skim milk powder. Other carriers which may be used include water, ethanol, a polyol (for example, glycerol, propylene glycol and liquid polyethyleneglycol and the like), vegetable oils and suitable mixtures thereof.

The present invention further contemplates a method for immunizing newly-hatched birds against infection by pathogenic microorganisms. The method further or alternatively provides for the development of an immune response to recombinant antigens. The method of the present invention is accomplished by the in ovo administration of an amount of one or more attenuated or avirulent modified microorganisms capable of inducing an immune response against the corresponding "wild-type" microorganism, to immunologically cross reactive microorganisms and/or to any heterologous or non-indigenous (e.g., recombinant) antigens expressed in the attenuated or avirulent modified microorganism. The modified microorganism may also competitively exclude other organisms in the tissues and/or generally promote the immune responsiveness of the avian host.

In a preferred embodiment, the attenuated or avirulent modified microorganism is capable at the inoculated amount of colonizing tissues in the bird either before or after hatching but without having a substantially adverse effect on hatchability and/or subsequent chick viability. According to this preferred aspect of the present invention, there is provided a method for inducing immunity in a newly-hatched bird to one or more pathogenic microorganisms, said method comprising administering in ovo an amount of attenuated or avirulent microorganism effective to colonize one or more tissues in said bird wherein said attenuated or avirulent microorganism carries a mutation (e.g., deletion, substitution or addition of nucleotides) in a gene encoding an enzyme required for chorismate biosynthesis in said microorganism.

The tissues preferably colonized include, but are not limited to, heart, liver, intestine, bursa of fabricus and airsac. For best results, the effective amount of inoculum is in the range of $10^2$–$10^{14}$ colony forming units (cfu) per egg. The amount of inoculum determines the extent of colonization and length of immune response after hatching and also varies due to the type of organism used. Preferred inocula include approximately $10^1$, $10^2$, $10^3$, $10^4$, $10^5$, $10^6$, $10^7$, $10^8$, $10^9$, $10^{10}$, $10^{11}$, $10^{12}$ and $10^{13}$ cfu/egg. Even more preferred inocula include approximately $10^2$–$10^{10}$ cfu/egg. The most preferred inoculum is in the range $5\times10^2$–$5\times10^4$ cfu/egg. Best results are obtained when the vaccine is inoculated into the air sac where the microorganism of the vaccine proceeds to colonize the air sac side of the air sac membrane. Prior to hatching, the embryo punctures the air sac membrane and is exposed to the microorganism, which then proceeds to colonize one or more tissues in the embryo before, during and/or after hatching.

The attenuated or avirulent microorganism is generally inoculated into the egg generally in the last half of the incubation term. For example, in the case of chickens, eggs are generally inoculated from about incubation day 12 to about incubation day 20. Preferably, the inoculation occurs from between day 14 to about day 19. More preferably, the chicken eggs are inoculated at about day 15–18. For duck eggs, the preferred inoculation times are from about day 16 to about day 27, more preferably, from about day 18 to about day 26 and even more preferably from about day 22 to about day 24.

The present invention also extends to fertilized eggs inoculated with the vaccine prior to incubation. The eggs are conveniently packaged for sale with or without instructions for subsequent incubation.

According to this aspect of the present invention, there is provided a fertilized egg from a poultry bird having an air sac wherein the air sac is inoculated with a modified microorganism which:

(a) exhibits auxotrophy to one or more growth factors such that it is incapable of growing on a minimal medium in the absence of said one or more growth factors; and (b) is capable of colonizing one or more tissues in an embryo prior to hatching after the embryo breaks through the air sac; and (c) is capable of inducing an immune response in the embryo before or immediately after hatching against a virulent form of said microorganism or an immunologically cross-reactive microorganism or virulent organism or virus carrying an antigenic determinant expressed by said avirulent microorganism.

Administration of the inoculum is conveniently by injection and generally injection into the air sac. The organism colonizes the air sac and the bird is exposed to the organism after breaking through the air sac prior to hatching. The bird may then take in the organism via the respiratory and/or oral tracts. Notwithstanding that the air sac is the preferred route of in ovo administration, other regions such as the yolk sac or chorion allantoic fluid may also be inoculated by injection. In the case of inoculation into the yolk sac or other fluids, a lower inoculum is generally favored and/or an attenuated or avirulent organism with a reduced growth rate is used so as to decrease embryonic death. In any event, the hatchability rate might decrease slightly when the air sac is not the target for the inoculation although not necessarily at commercially unacceptable levels. The mechanism of injection is not critical to the practice of the present invention, although it is preferred that the needle does not cause undue damage to the egg or to the tissues and organs of the developing embryo or the extra-embryonic membranes surrounding the embryo.

Generally, a hypodermic syringe fitted with an approximately 22 gauge needle is suitable. The method of the present invention is particularly well adapted for use with an automated injection system, such as those described in U.S. Pat. Nos. 4,903,635, 5,056,464 and 5,136,979.

The present invention is particularly well suited for the protection of poultry birds such as chickens from infection by Salmonella species. In accordance with the preferred aspect of the present invention there is provided a live in ovo vaccine for poultry birds comprising an attenuated Salmonella which:

(a) exhibits auxotrophy for one or more growth factors such that it is incapable of growing on a minimal medium in the absence of said one or more growth factors;

(b) is capable of colonizing one or more tissues in an embryo prior to hatching; and (c) is capable of inducing before or immediately after hatching an immune response in the embryo against a virulent form of said Salmonella or an immunologically cross-reactive Salmonella or a virulent organism or virus carrying an antigenic determinant expressed by said avirulent Salmonella.

Preferably, the vaccine is adopted for inoculation into the air sac such that the embryo is substantially exposed to the vaccine after breaking through the air sac. Preferred Salmonella species for use as the modified microorganisms are *Salmonella typhimurium, Salmonella paratyphi* A or C, *Salmonella schottmulleri, Salmonella choleraesuis, Salmonella montevideo, Salmonella newport, Salmonella enteritidis, Salmonella gallinarum, Salmonella pullorum, Salmonella abortusovi, Salmonella abortus-equi, Salmonella dublin, Salmonella sofia, Salmonella havana, Salmonella bovismorbificans, Salmonella hadar, Salmonella arizonae* and *Salmonella anatum.* More preferably, the modified microorganism is *S. typhimurium* or *S. enteritidis.* Conveniently, the mutation is in the aromatic biosynthetic pathway such as in aroA, aroB, aroC or aroD. Most preferably, it is in aroA.

These and other aspects of the present invention are further exemplified by the following non-limiting examples.

EXAMPLE 1

*Salmonella typhimurium* STM-1

Origin

The parent wild-type strain of *S. typhimurium* was isolated from a chicken flock infected by Salmonella species at the Veterinary Research Institute, Parkville, Victoria, Melbourne, Australia. The isolate was stored as a frozen culture. Mutant strain *S. typhimurium* LTD strain 1545 (aroA Tn:10) was sourced from Dr J Roth, University of Utah, USA. The STM-1 mutant was generated by phage transduction using P22 transduction of aroA Tn:10 from strain 1545 to the wild-type *S. typhimurium* isolated from the chicken flock. Transposon Tn:10 insertion mutants were selected and then a transposon deleted aroA deleted mutant isolated. This mutant was designated *S. typhimurium* STM-1 and a sample was deposited at the Australian Government Analytical Laboratories, 1 Suakin Street, Pymble, New South Wales, 2037, Australia, and has been assigned Accession number N93/43266 on Oct. 25, 1993.

Media

Tryptic soy broth (TSB) supplemented with yeast extract (1% w/v) is used both for the preparation of seed cultures and for production of live vaccine. TSB contains digests of casein and soyabean meals, together with dextrose, sodium chloride and dipotassium phosphate. The medium is sterilized by autoclaving at 121° C. prior to use. Skim milk is employed as a cryoprotectant for freeze drying.

The growth medium containing casein is sterilized by autoclaving at 121° C. prior to use. Australian derived skim milk powder is used in the freeze drying of the vaccine. This material is received in non-sterile condition and dispatched to Ansell-Steritech facility in Sydney, Australia, for gamma irradiation at 2.5 megarads prior to use.

Powdered growth media are dissolved in distilled water and sterilized at 121° C. for at least 15 minutes. Skim milk powder is packed into 1 kilogram quantities in cardboard boxes for gamma irradiation at 2.5 megarads. "Released Sterile" stickers are applied on return from gamma irradiation after ensuring that the gamma irradiation indicators have changed colour during sterilization. Sterilized skim milk is mixed by stirring with the culture after fermentation and concentration prior to lyophilization.

Characteristics of *S. typhimurium* STM-1

*Salmonella typhimurium* STM-1 is $aroA^-$ and $ser^-$. The organism will not grow on minimal media. STM-1 has a growth profile consistent with an aroA deletion organism requiring both paraaminobenzoic acid (PABA) and parahydroxbenzoic acid (PHBA) for growth. The insertion of the Tn:10 transposon, and its subsequent deletion near the aroA gene of STM-1, resulted in another mutation along the serine biosynthetic pathway. This is supported by the lack of growth on minimal media supplemented with all the end products of the aromatic pathway with growth occurring only when serine or either glycine and cystine is added to the media. The serine deletion does not limit growth of the mutant in vivo.

STM-1 can be easily distinguished biochemically from its parent strain and related strains by being $H_2S$ negative. Growth of STM-1 on XLD agar is indicated by the appearance of pink colonies. Growth on MacConkey's agar is seen as clear lac negative colonies of characteristic Salmonella appearance.

STM-1 strain is, in common with its parent, streptomycin resistant, novobiocin resistant and fusaric acid resistant. It differs from the parent strain in showing greater susceptibility to penicillin and sulfafurazole.

Serologically, STM-1 colonies and broths test positive for poly "O" antigen and Group B salmonella antigens.

The STM-1 microorganism has the same detectable plasmid composition as its wild-type parent, with plasmids at 23 Kb, 27.5 Kb (see FIG. 1) and two larger plasmids in the 60 to 100 Kb range. Both the wild-type and STM-1 express the 11 KDa cryptic plasmid.

Figure 2:
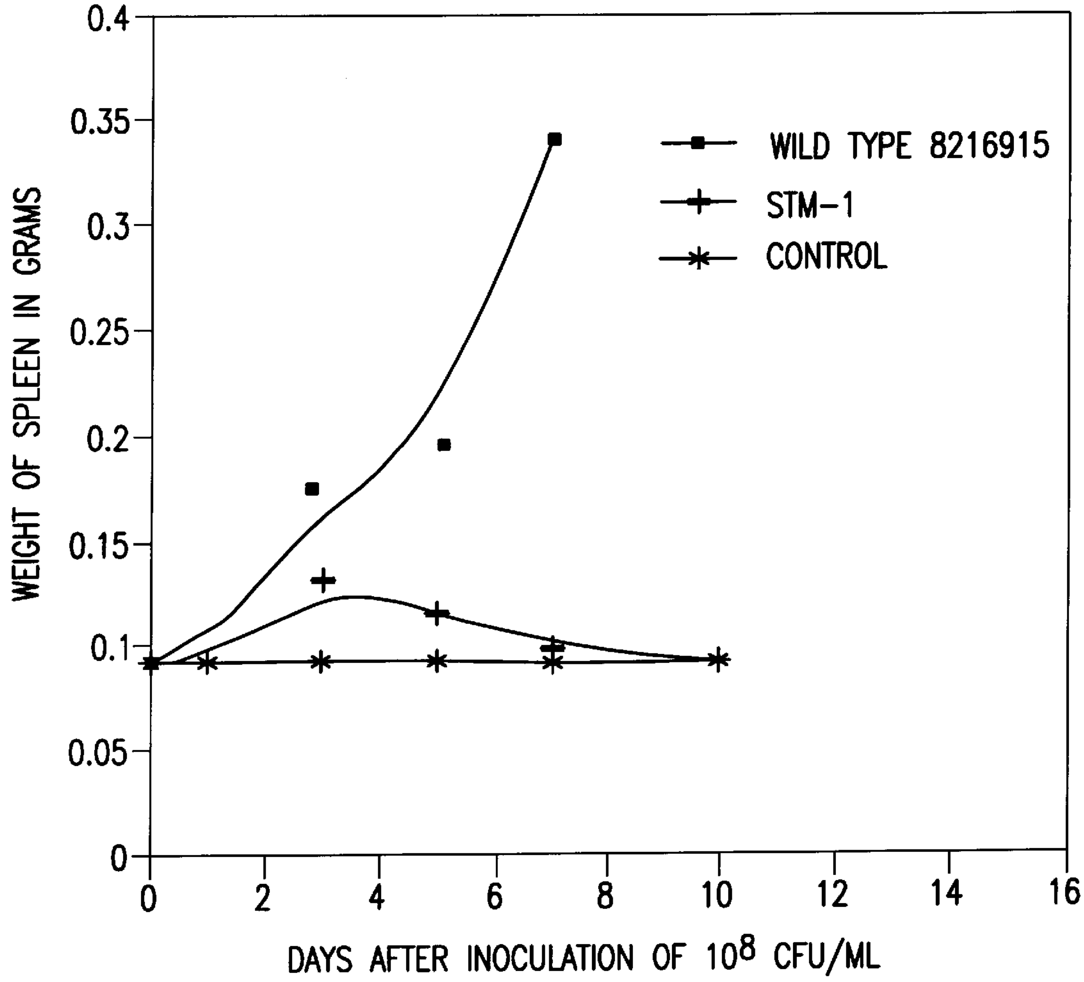
FIG. 2 is a graphical representation of splenomegaly induced by *S. typhimurium* STM-1 and its wild-type parent wild-type; STM-1; control.
Figure 3:
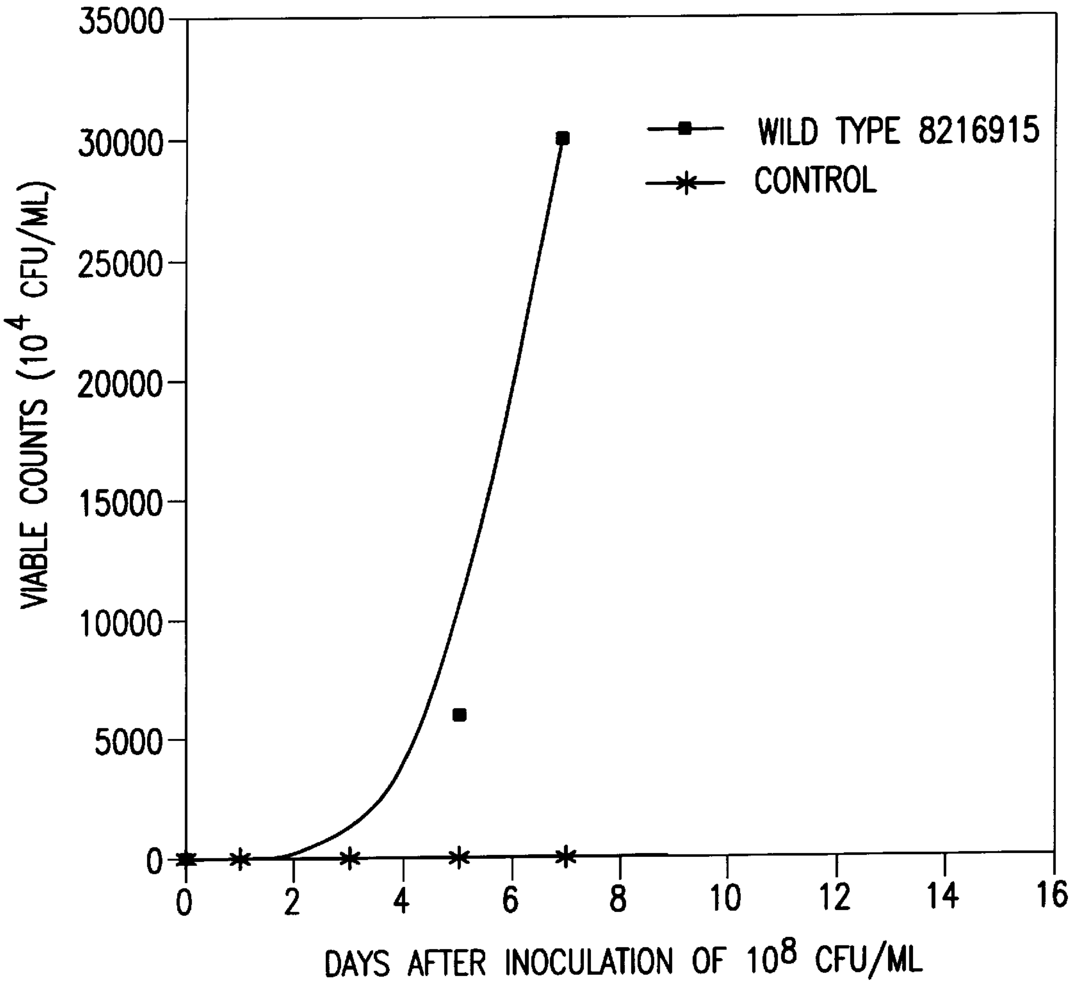
FIG. 3 is a graphical representation of viable counts in the spleen of mice infected with wild-type *S. typhimurium.* wild-type; control.
Figure 4:
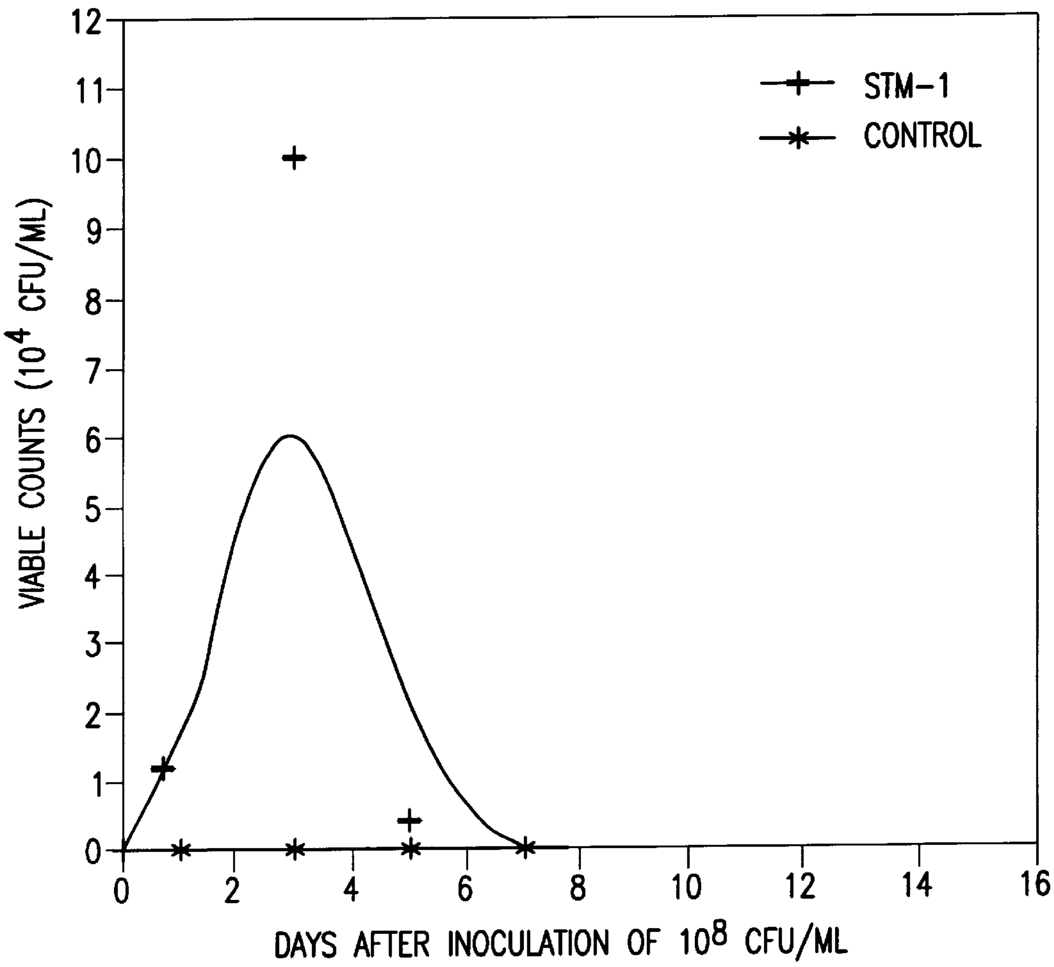
FIG. 4 is a graphical representation of viable counts in the spleen of mice infected with *S. typhimurium* STM-1. STM-1; control.
Figure 5:
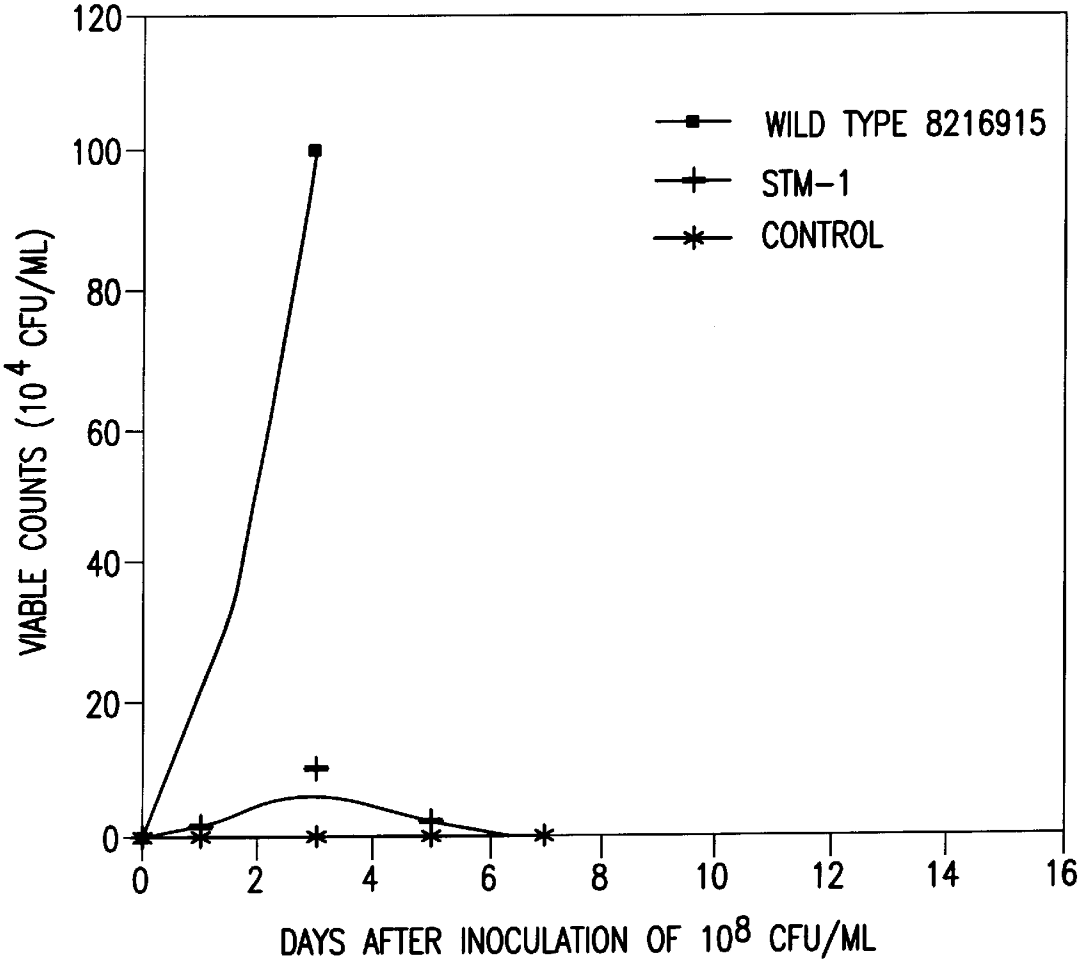
FIG. 5 is a graphical representation of viable counts in the spleen of mice infected with *S. typhimurium* STM-1 and its wild-type. wild-type; STM-1; control.

*Salmonella typhimurium* STM-1 is virtually non-virulent, being over 10,000 times less virulent than its parent. A comparison between the invasion capability of the wild-type parent and STM-1 indicated in a mouse model that the mutant strain is capable of invading and even persisting in the spleen for a few days without causing clinical illness (FIG. 2). Throughout the 10 day period, none of the STM-1 infected mice died and all looked healthy as judged by the texture of their coat. In contrast, by day 5 post infection, all wild-type mice showed signs of hunching and loose unhealthy coat texture. By day 8 post infection, all wild-type infected mice were dead. There was multiplication of wild-type strain in the spleen of wild-type infected mice where viable counts exceeded that of the inoculum dose by day 6, whereas those of STM-1 never reached a count of higher than $10^5$ CFU/ml. Results are shown in Table 1.

TABLE 1

| DAYS AFTER INOCULATION OF BACTERIA | Wild-type 08216915 | MUTANT STM-1 |
|---|---|---|
| Day 1 | 0.09615 (1.06x) | 0.0923 (1.014x) |
| Day 3 | 0.17205 (1.99x) | 0.13085 (1.44x) |
| Day 5 | 0.1944 (2.14x) | 0.11555 (1.27x) |
| Day 7 | 0.339 (3.74x) | 0.0977 (1.07x) |
| Day 10 | All dead | 0.0910 |

( ) represents increase in spleen size compared to that of control mice.

Mice vaccinated orally or intraperitoneally with STM-1 and then challenged with the wild-type strain at $10\times LD_{50}$ were protected against salmonellosis. Splenomegaly data was recorded for a period of 10 days after inoculation. Splenomegaly was marked in wild-type infected mice, whereas it was mild, reaching a peak at day 3 and declining rapidly to its normal size by day 10 in STM-1. The control strain showed no increase in spleen size. FIGS. 2 to 5 compare the growth characteristics of both STM-1 and wild-type strain.

In accordance with this invention, STM-1 has been used in extensive chicken trials administered by oral, subcutaneous (SC) and intraperitoneal (IP) routes. Oral titres up to $1.2\times10^{10}$ have been applied and found not to cause ill effect. Indeed, vaccinated birds have been shown to be consistently and significantly heavier than corresponding inoculated control chickens.

EXAMPLE 2

Preparation of Master and Production Seeds

*Salmonella typhimurium* STM-1 cultures are grown as follows. A culture is used to inoculate 100 ml of growth medium containing TSB supplemented with 1% w/v yeast extract. The broth is incubated at 37° C. overnight with shaking. The culture is confirmed as pure by Gram stain, growth on blood agar, growth on XLD agar, MacConkey's agar and triple sugar iron (TSI) broth. The culture is lyophilized in the presence of sterile skim milk such that each ampoule contains $10^9$ organisms. This is the Master seed.

An ampoule of Master seed is then used in the same processes to produce a production seed lot. Ampoules of Master and production seed are stored at −20° C.

EXAMPLE 3

Preparation of Vaccine

Two ampoules of production seed are used to inoculate two aspirator bottles, each containing approximately 500 ml of growth medium (TSB plus yeast extract) to initiate the growth process. Each 500 ml culture is used to inoculate approximately 10 liters of growth medium in a pyrex carboy. The carboys are in turn used to inoculate a production fermenter. All manipulations up to the carboy culture stage are performed aseptically in a biohazard cabinet or laminar flow cabinet. Transfer of the carboy cultures to the fermenter is achieved through steam sterilized tubing/hard plumbing connection.

After 6–8 hours, the inoculum is transferred provided that it is thickly turbid and microscopically pure by Gram stain and purity plates. The cultures are connected to a stainless steel fermenter via a steam sterilized connection and used to inoculate the fermenter contents. The optical density is used to monitor culture growth in the fermenter. At peak density, the culture is passed through a continuous flow centrifuge to achieve concentration of the biomass and re-checked for purity. The culture is chilled during the process. The chilled concentrate is blended with sterile skim milk powder and the mixture is filled into pharmaceutical grade glass bottles ready for freeze drying. Sterile dry nitrogen gas is used to back fill the bottles at the end of the lyophilization cycle prior to closing with rubber stoppers and removal from the freeze drier. An aluminium donut seal is affixed to each bottle. Bottles are subsequently labelled and packed into cartons for dispatch. Prior to release, the vaccine is tested for potency, safety, moisture, purity and identity.

EXAMPLE 4

Safety and Efficacy of the Vaccine

Data on the lack of virulence of STM-1 are provided in Example 1. A series of experiments addressing both oral and subcutaneous injection of STM-1 is set out below demonstrating both the safety and efficacy of the organism.

Experiment 1

A dose response experiment was designed to ascertain the dose range of STM-1 required orally to produce strong antibody (IgG) responses in chicken sera without adversely affecting chickens. There were four groups of 25 chickens: a control group that received 100 ml of phosphate-buffered saline (PBS) (0.145 M NaCl, 0.01 M sodium phosphate [pH 7.1]) per chicken, and three inoculated groups that received $10^4$, $10^6$, or $10^{10}$ STM-1 per chicken. These chickens were inoculated at 1 day of age. Blood was taken from 5 chickens in each group at 7, 14, 21 and 28 days after inoculation. Sera obtained from these bloods were examined for humoral responses to sonicated STM-1 in an enzyme linked immunosorbent assay (ELISA). Low doses ($1\times10^4$) of the bacterium produced no significant IgG responses, intermediate doses ($1\times10^6$) produced significant responses in birds 21 and 28 days post-inoculation and high doses ($1\times10^{10}$) produced significant responses in chickens 7, 14, 21 and 28 days post-inoculation.

Experiment 2

Information gathered in Experiment 1 was used to examine IgG, IgM and IgA responses in sera and gut washings from chickens inoculated orally and subcutaneously with $10^9$ STM-1. This examination of humoral responses in orally and subcutaneously inoculated chickens was to provide information on the level of antibody responses elicited by these routes of inoculation. Four groups of chickens were inoculated at 1 day of age. Two groups of 30 chickens were inoculated with STM-1, one orally and the other subcutaneously. Two other groups of 22 chickens received PBS orally or subcutaneously. Blood was taken from 5 chickens in each group at 7, 14, 21 and 28 days post-inoculation. Fecal swabs were taken from the orally inoculated chickens on the same days as the bloods before all chickens were killed and intestine removed for preparation of gut washings. The sera and gut washings from these chickens were examined for IgG, IgM and IgA responses to STM-1 antigens by ELISA.

No antibody responses were detected in sera or gut washings from 7-day-old chickens. The first statistically significant antibody responses detected were IgG responses to sonicated STM-1 and IgM responses to STM-1 lipopolysaccharide (LPS) in sera from 14-day-old chickens. The first significant IgA responses to STM-1 LPS were detected in sera from 21-day-old chickens. Antibody responses in gut washings from orally inoculated chickens were restricted to IgG and IgA, with the response detected being an IgG response to STM-1 LPS in gut washings from 21-day-old chickens. Interestingly, no significant IgM response was detected to STM-1 porins in sera or to any of the STM antigens in gut washings.

Figure 6:
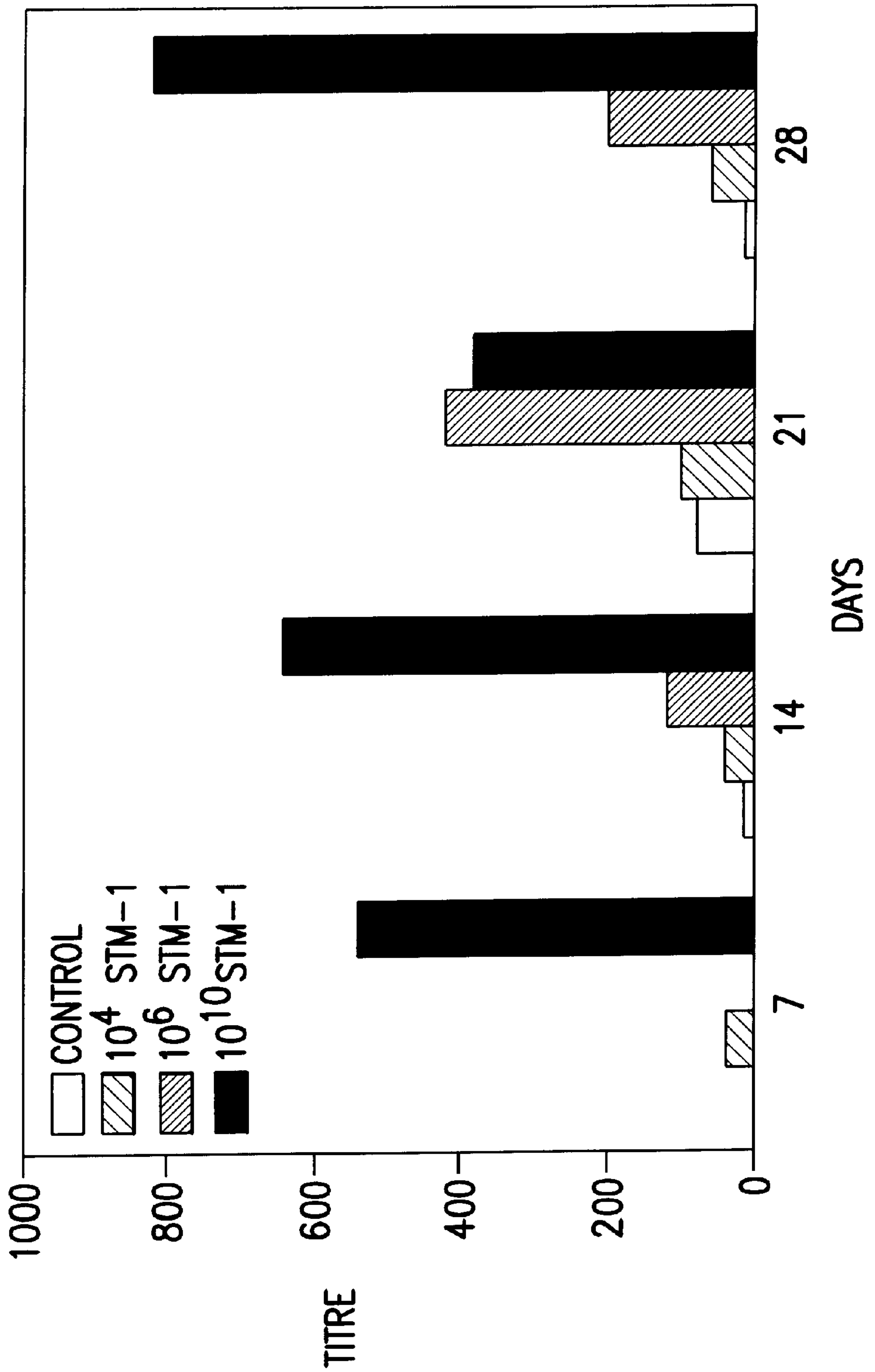
FIG. 6 is a graphical representation of antibody titre (IgG) in chickens inoculated with *S. typhimurium* STM-1.
Figure 7:
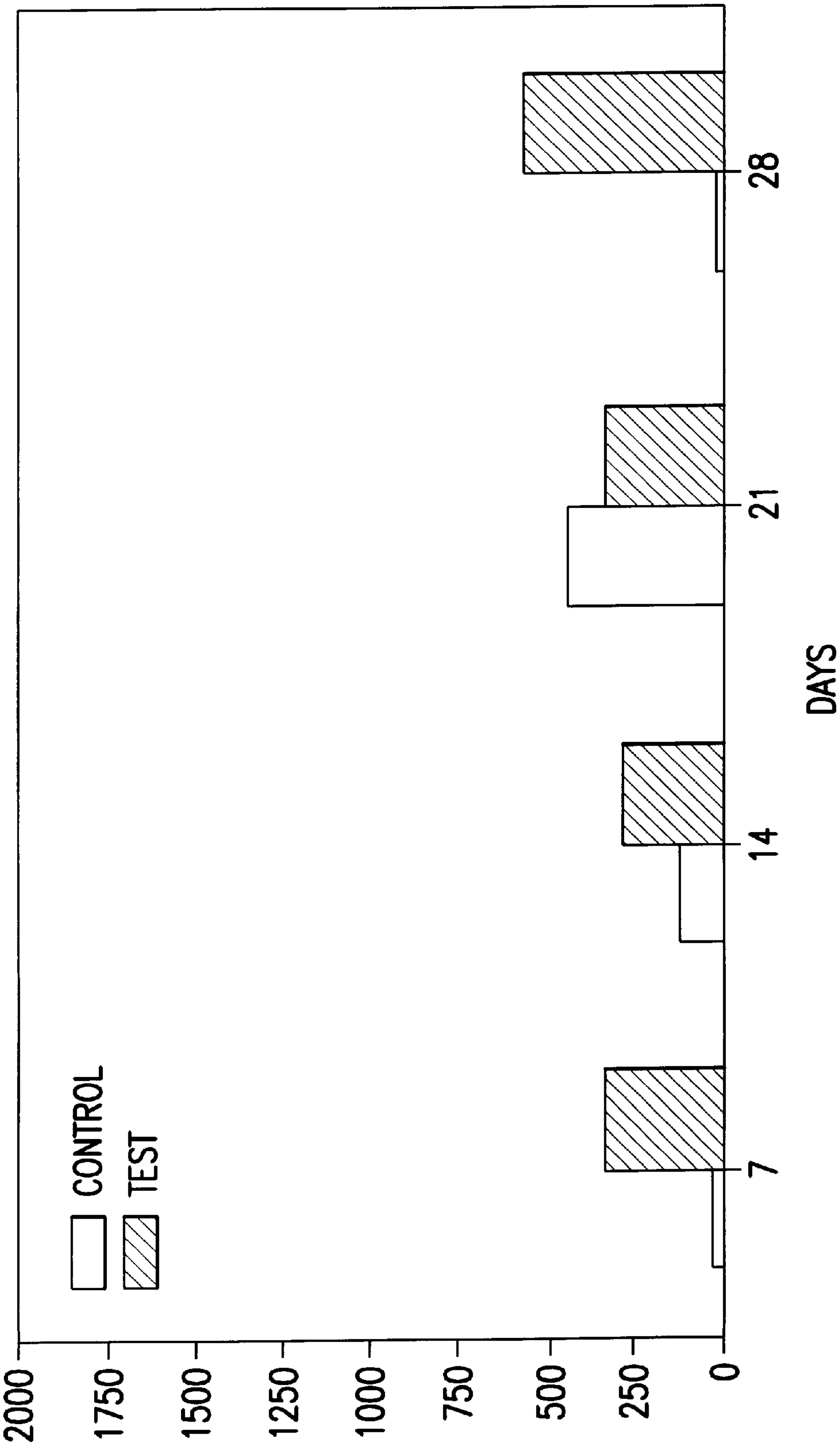
FIG. 7 is a graphical representation of antibody titre in chicken following oral inoculation with *S. typhimurium* STM-1.
Figure 8:
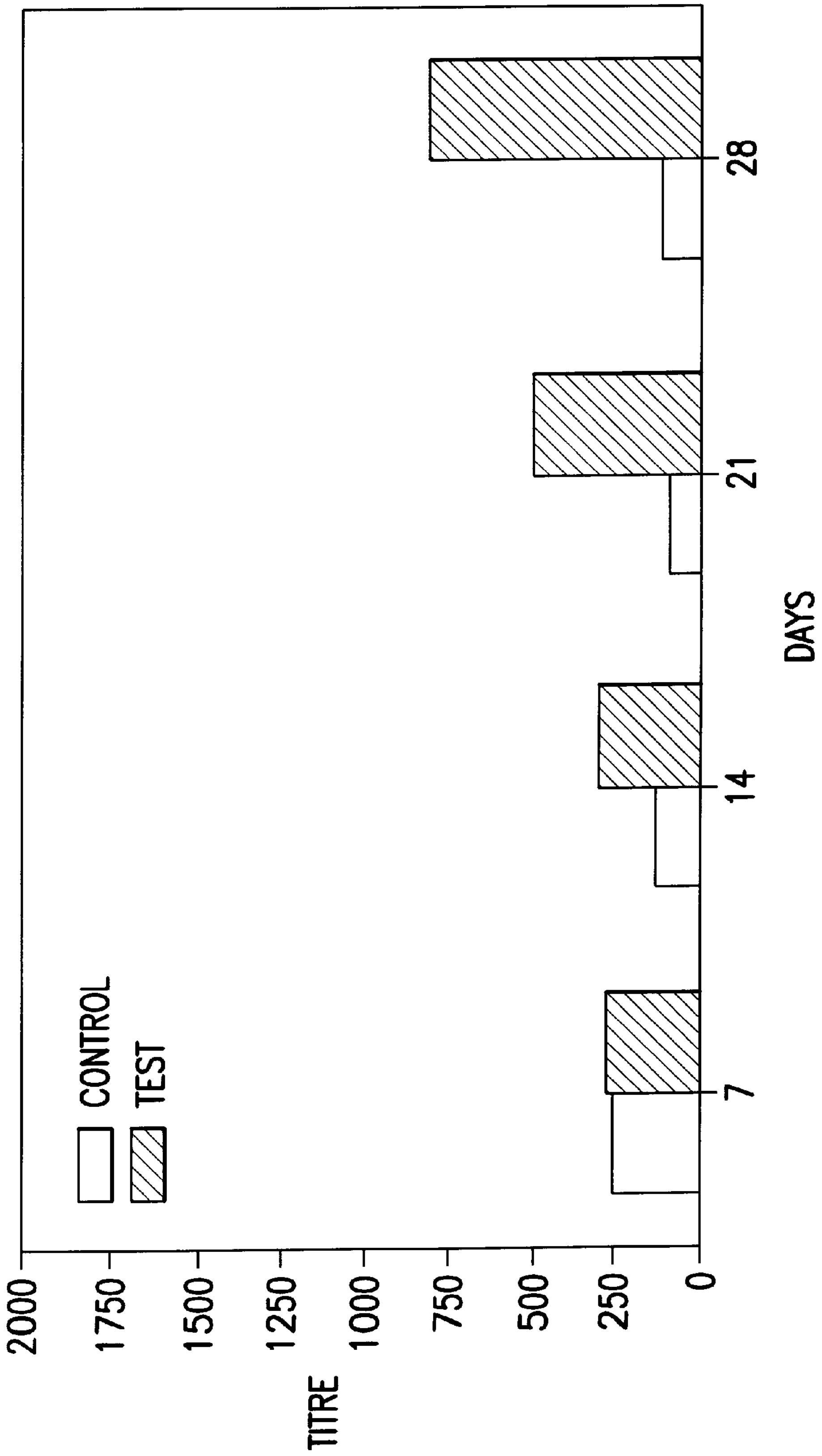
FIG. 8 is a graphical representation of antibody titre in chickens following oral inoculation with *S. typhimurium* STM-1.
Figure 9:
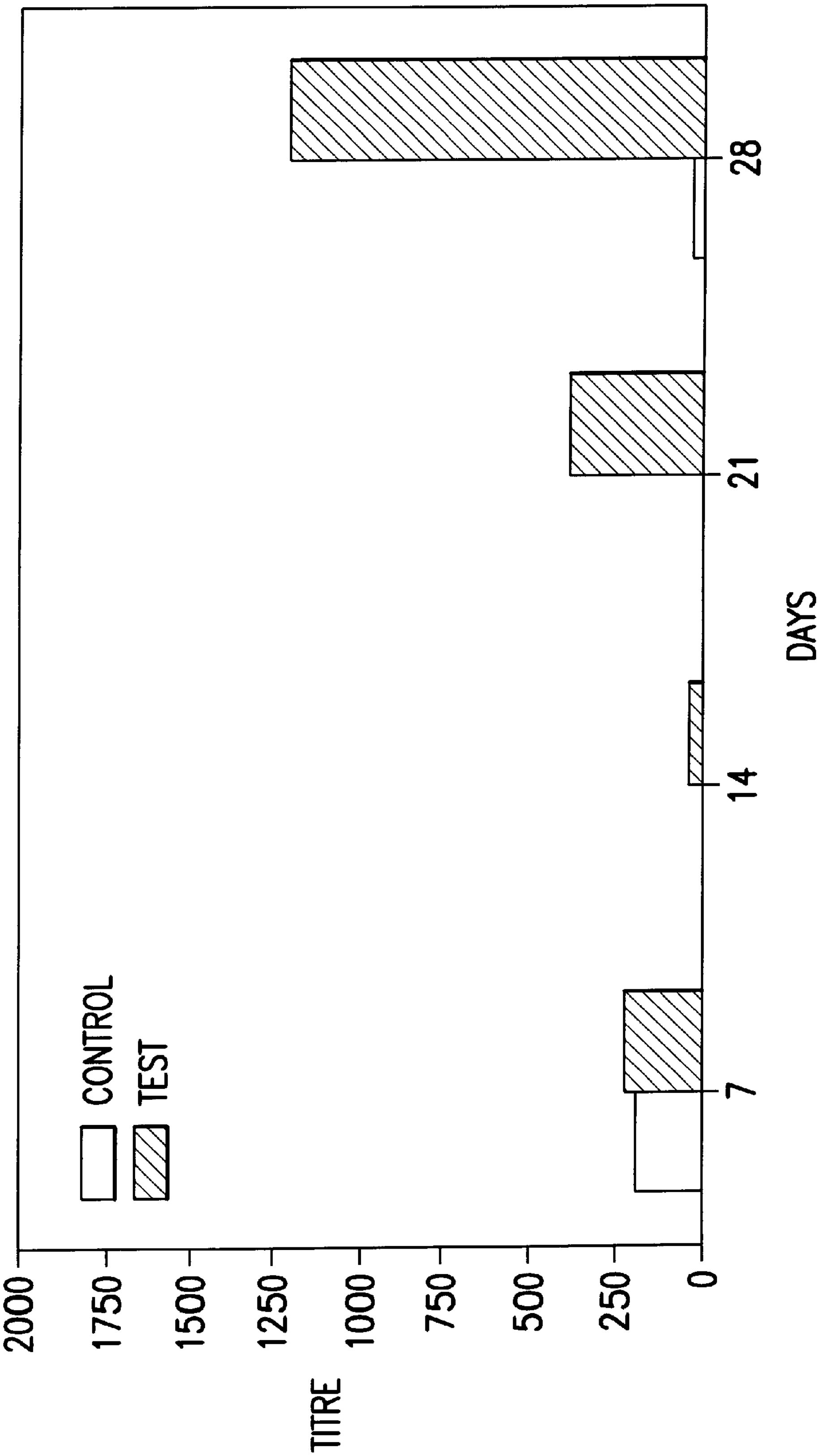
FIG. 9 is a graphical representation of antibody titre in chickens following subcutaneous inoculation with *S. typhimurium* STM-1.
Figure 10:
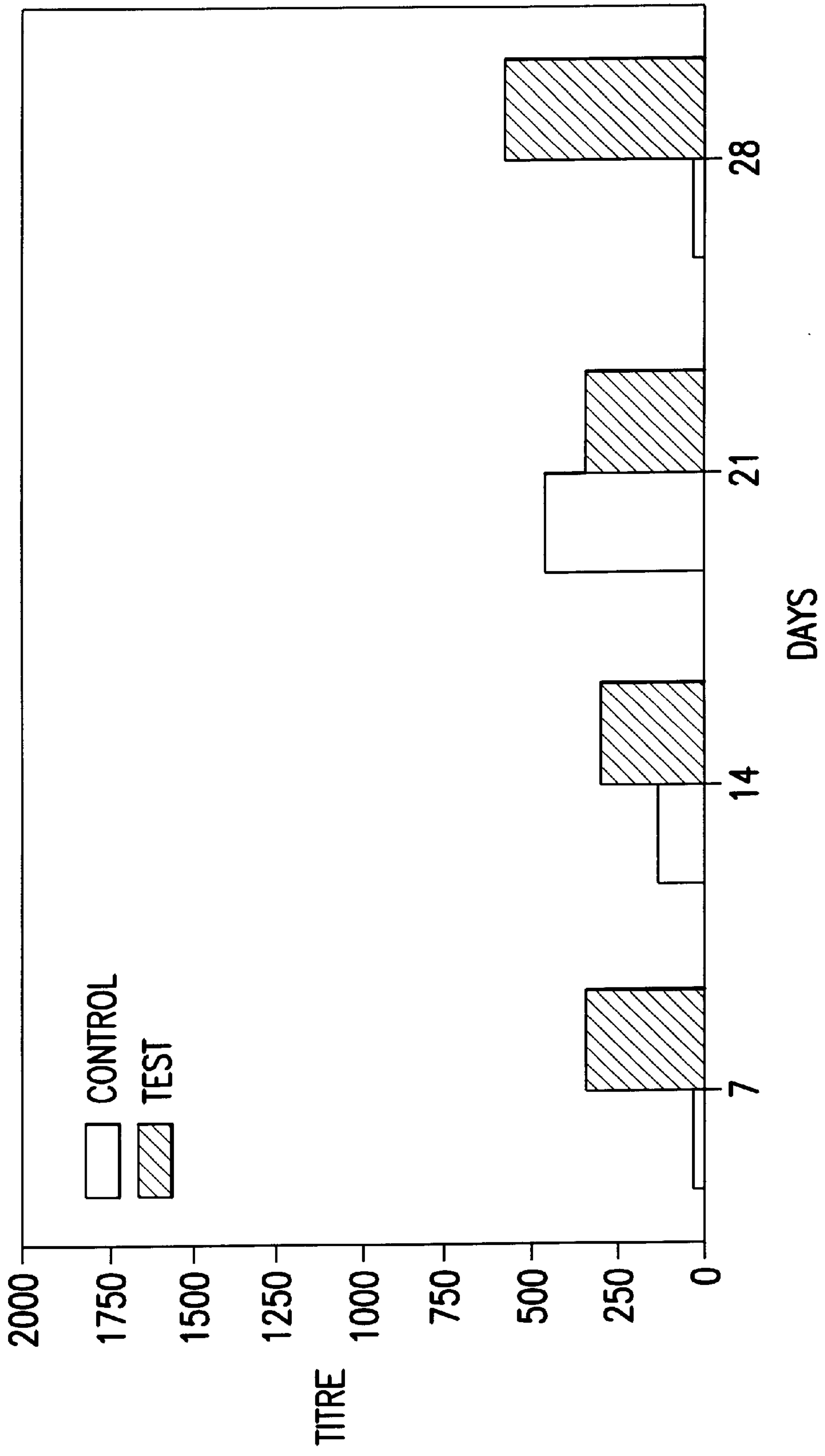
FIG. 10 is a graphical representation of antibody titre in chickens following subcutaneous inoculation with *S. typhimurium* STM-1.

Table 2 and FIGS. 6, 7, and 8 summarize these findings. Table 2 and FIGS. 9 and 10 also show humoral responses in chickens immunized subcutaneously with STM-1.

TABLE 2

| Age of | | Responses in sera | | | | | | | | | Responses in gut washings | | | | | | | | |
|---|---|---|---|---|---|---|---|---|---|---|---|---|---|---|---|---|---|---|---|
| chickens | Route of | IgG | | | IgM | | | IgA | | | IgG | | | IgM | | | IgA | | |
| (days) | Inoculation | sc | por | lps | sc | por | lps | sc | por | lps | sc | por | lps | sc | por | lps | sc | por | lps |
| 7 | Oral | – | – | – | – | – | – | – | – | – | – | – | – | – | – | – | – | – | – |
| 14 | | + | – | – | – | – | + | – | – | – | – | – | – | – | – | – | – | – | – |
| 21 | | – | – | + | + | – | + | – | – | + | – | – | – | – | – | – | – | – | – |
| 28 | | + | – | + | + | – | + | + | + | + | + | – | + | – | – | – | + | – | + |
| 7 | Subcutaneous | – | – | – | + | – | – | – | – | – | – | – | – | – | – | – | – | – | – |
| 14 | | – | + | + | – | + | – | – | – | – | – | – | – | – | – | – | – | – | – |
| 21 | | – | + | + | + | + | + | – | + | – | – | – | – | – | – | – | – | – | – |
| 28 | | + | + | + | + | + | + | + | + | + | – | – | – | – | – | – | – | – | – |

A Antigens are sonicated STM (sc), STM porins (por) and STM lipopolysaccharide (LPS).
+ = antibody response in inoculated chickens that are significantly different ($P \leqq 0.05$) from those in control chickens.
– = antibody response in inoculated birds that are not significantly different ($P \leqq 0.05$) from those in control chickens.

The first statistically significant IgG, IgM and IgA responses were detected in sera from 14-, 7- and 21-day-old chickens. IgM responses were directed against all three antigens, including STM porins. No antibody responses were detectable in gut washings. High IgG responses to STM-1 porins in gut washings and IgM responses to STM-1 porins in sera were seen in 28-day-old control chickens. However, this elevation in levels of antibody responses was not detectable when STM-1 LPS was used as the antigen in the ELISA.

Chickens vaccinated with $1 \times 10^8$ STM-1 subcutaneously and challenged subcutaneously 7 days later with $1 \times 10^8$ virulent *S.typhimurium* all survived the challenge, whereas a non-vaccinated group also challenged subcutaneously with $1 \times 10^8$ virulent *S. typhimurium* all died. Chickens orally vaccinated with STM-1 prior to oral challenge with a virulent *S. typhimurium* stopped excreting the organism before non-vaccinated chickens. No chickens died during the experiment, but all excreted the virulent organism post-challenge. However, by 35 days post-challenge, fecal swabs showed that all vaccinated chicken ceased to excrete the virulent organism, but 10 out of 30 non-vaccinated chickens were still excreting the organism.

EXAMPLE 5

Effect of *S. typhimurium* STM-1 on Weight Gain

To examine the effect of an oral inoculation of STM-1 on the weight gain of chickens, the chickens were orally inoculated and weighed. The results are shown in Table 3.

Oral inoculation of chickens with $1 \times 10^9$ or $5 \times 10^9$ STM-1 did not adversely affect the weight gain of the chickens, as the inoculated chickens had significantly greater weights than controls at the same age. The weight gain experienced at the laboratory level and shown in Table 3 was also seen in the field trials.

TABLE 3

Body Weight and Mortality of Broiler Chickens Vaccinated with STM-1 via the Drinking Water at Day Old

| | Shed 1 (10,000 birds, vaccinated) | | Shed 2 (15,000 birds, non-vaccinated | |
|---|---|---|---|---|
| Age | Bodyweight (g) | Mortality (%) | Bodyweight (g) | Mortality (%) |
| 0 | 43 | | 43 | |
| 7 | 135 | 1.57 | 128 | 2.47 |
| 14 | 352 | 2.10 | 348 | 4.58 |
| 21 | 655 | 2.42 | 660 | 5.00 |
| 28 | 1041 | 2.89 | 1067 | 5.44 |
| 35 | 1410 | 3.59 | 1420 | 5.93 |
| 42 | 1792 | 4.03 | 1697 | 6.11 |

EXAMPLE 6

Spread and Persistence of the Vaccine Strain

The vaccine has been shown to spread to birds when the birds are maintained in high density housing. Investigations into the spread of STM-1 within a group of chickens in the laboratory, of which only 2 were inoculated, revealed the organism spread rapidly when the group was in close proximity and maintained on solid flooring. Examination of fecal swabs revealed that all chickens were excreting the organism within 5 days, but that the organism was eliminated from the chickens by day 14.

However, under field conditions, where flooring is varied and bird distance greater, there was significantly reduced bird to bird transmission. Indeed, the rate of bird to bird transmission was inadequate for inducement of a protective response. Only 60% of the in-contact birds in pen trials showed STM-1 spread, but not at adequate levels to provide a protective response.

STM-1, if administered to chickens at 1 day of age, cannot be isolated after day 28 in the laboratory. Fecal swabs taken on days 7, 14, 21 and 28 post-inoculation revealed orally inoculated chickens were excreting the organism only at the first two sampling times tested. Field results showed a similar pattern.

Set out in Table 4 are the STM-1 isolation rates on a 30,000 bird field trial.

Table 4

| Age | Culture | Number of samples | Shed One (Vaccinated) | Shed Two (control) |
|---|---|---|---|---|
| | | | *S. typhimurium* STM-1 isolation rates expressed as Number of STM-1 | |
| 1 | Liver[1] | 20 | 0/10 | 0/10 |
| 2 | Liver | 20 | 3/10[2] | 0/10 |
| | Faeces | 30 | 29/29[4] | not tested |
| 3 | Liver | 20 | 0/10 | 0/10 |
| 4 | Liver | 20 | 1/10[3] | 0/10 |
| 5 | Liver | 20 | 0/10 | 0/10 |
| 6 | Liver | 20 | 0/10 | 0/10 |
| 7 | Liver | 20 | 0/10 | 0/10 |
| | Faeces | 30 | 7/30[5] | not tested |
| 28 | Faeces | 60[5] | 0/30[6] | 0/30[6] |
| 43 | Half caeca | 60 | 0/30[7] | 0/30[8] |

[1]only livers from mortalities cultured direct and through broth culture enrichment
[2]positive on direct culture and enrichment
[3]positive on Selenite enrichment only
[4]one sample discarded due to abnormal overgrowth
[5]caecal squirt droppings selected from shed floor
[6]Vaccinated shed and control shed: from each 4 organisms identified as *Salmonella sofia* were isolated. No STM-1 was found.
[7]From vaccinated shed 3/30 *Salmonella sofia*
[8]From control shed 6/30 *Salmonella sofia*

Results of environmental swabbing and STM-1 isolations from one test pen and two commercial broiler shed trials showed STM-1 did not persist in the environment or in the birds beyond 21 days post-vaccination.

STM-1 was continually passaged in TSB with 1% w/v yeast extract for 10 consecutive passages. An aliquot of 10 ml of culture was added to 500 ml of fresh prewarmed culture medium and incubated overnight at 37° C. This process was undertaken daily for 10 consecutive days. At each passage, culture was evaluated for purity, presence of aroA deletion and cell number. The cell density at each passage was approximately $5\times10^9$/ml. At the completion of 10 passages, the organism was confirmed to be STM-1. Due to the inability of the organism to adequately direct passage in sufficient numbers past the third in contact bird to bird passage, a protocol inclusive of enrichment between passages is utilized for chicken back passaging. The STM-1 at a cell density of $5\times10^9$ was inoculated orally into a 24 day old chicken. After 24 hours, faecal swabs were collected, enriched in selenite broth and STM-1 selected. The STM-1 re-isolate was then grown overnight at 37° C. in TSB plus 1% w/v yeast extract and $5\times10^9$ (approximately 1 ml of overnight culture) inoculated into bird 2 (and so on) for 10 passages. Isolates obtained at each passage and any Salmonella-like isolates were fully characterized (no Salmonella variants were found) and the final isolates confirmed to be STM-1.

The present studies indicate that STM-1 can be used as a means of controlling salmonellosis and as a presentation vehicle for antigens from enteric pathogens. Colonization of the gut ensures that the selected antigens remain accessible to the host defense mechanisms for a long period. The lack of adverse effects seen even with high inoculation doses ($1.2\times10^{10}$) and the possible growth promoting effect of the bacterium indicates that STM has potential as a probiotic.

EXAMPLE 7

Colonization of "Pre-Hatch" and "Post-Hatch" Organs of Chickens by *Salmonella typhimurium* Mutant STM-1 After Air Sac Vaccination at 18 Days of Incubation in ovo The object of this experiment was to determine the colonization of tissues and fecal shedding of STM-1 at different levels of vaccination at day 18 following in ovo administration.

Sixteen day incubated eggs were maintained in an incubator with regular turning 2 times daily. Newly-hatched chickens were reared in individual groups under standard infra-red chicken rearing lamps. Water was available ad libitum and chemotherapy-free feed was used. At incubation day 18, the chicken embryos were vaccinated in ovo with either $10^8$ colony forming units (cfu) or $10^4$ cfu of *S. typhimurium* STM-1 growing cultures. Administration was by direct inoculation into the air sac of the egg. In another trial, $10^6$ cfu or $10^4$ cfu of the STM-1 mutant were administered to the egg.

Results

The hatched chicks, whether inoculated with $10^4$, $10^6$, or $10^8$ cfu shed the vaccine strain for the first three days post-hatching. Between 3 and 12 days, there was significant shedding from the chicks vaccinated with the STM-1 strain. The STM-1 mutant was cultured from all organs of all chicks given $10^8$ cfu per egg for up to 8 days and the majority of chicks given $10^4$ and $10^6$ cfu per egg. By way of example, 4 day chicks (five chicks) derived from eggs inoculated with $10^4$ cfu STM-1 showed colonization of the following tissues:

4/5 heart

5/5 liver

5/5 intestine

5/5 caecum

These results indicate that the mutant STM-1 can be administered at day 18 to the egg at from $10^4$–$10^8$ cfu per egg with no adverse effect on hatchability and subsequent chick viability. After in ovo vaccination at day 18, the organism colonized a wide range of organs and tissues in the chicken and there was shedding of the organism for a period of at least 8 days post-hatching.

EXAMPLE 8

Efficacy of in Ovo Administration of STM-1 against Subcutaneous Challenge by Virulent *Salmonella typhimurium*

The objective of this experiment was to determine if in ovo vaccination with STM-1 protects chicks from the clinical effects of *S. typhimurium* given subcutaneously at 7 days post-hatching.

Materials and Methods

The primary criterion for efficacy is mortality. Secondary measurements include differential fecal shedding and organ colonization.

Eggs were vaccinated on the eighteenth day of incubation with $10^4$ or $10^6$ STM-1 and chicks were challenged on the seventh day post-hatch with a dose 1 or 100 times greater than the $LD_{50}$ of wild-type *S. typhimurium.* For each vaccination dose, 2 groups of 10 birds were challenged with $10^6$ or $10^8$ cfu subcutaneously and a third group of 10 birds were left unchallenged. Three groups of 10 non-vaccinated birds were used as controls, 2 groups were challenged and 1 group left unchallenged. Health was monitored for all birds on a twice daily basis. Fecal shedding was monitored by culturing cloacal swabs for all birds on nominated days. Organ colonization was determined on all birds that died, and the surviving birds in each group were sacrificed and nominated organs were cultured on the fourteenth day after challenge.

The challenge strain was *Salmonella typhimurium* strain 82/6915.

The chicks received chemotherapy-free feed treated by gamma irradiation (Barastoc Stock Feeds, St Arnaud, Victoria, Australia) in 10 kg vacuum sealed multiwall paper and PVC containers. Each box was individually tested for the presence of Salmonella.

Hatched chicks were reared under infra-red heating lamps in accordance with general practice. Feed and water was available ad libitum throughout the trial period.

Forty eggs each were vaccinated with STM-1 with $10^4$ cfu per egg and $10^6$ cfu per egg, respectively, to ensure a minimum of 30 chicks per dose available for challenge at 7 days post-hatching.

Results

1. Hatchability

The rate of hatchability of eggs vaccinated with $10^6$ cfu per egg, $10^4$ cfu per egg and non-vaccinated eggs is shown in Table 5.

TABLE 5

| | Hatchability | | |
|---|---|---|---|
| | $10^6$ cfu/egg | $10^4$ cfu/egg | non-vaccinated |
| No. of eggs | 42 | 42 | 42 |
| No. hatched | 34 | 36 | 33 |
| % hatched | 81 | 86 | 79 |

2. Challenge with *Salmonella typhimurium* Non-vaccinated birds challenged with $10^8$ cfu per chick of wild-type *S. typhimurium* died rapidly in the first 72 hours. Ten out of 11 birds died. In the vaccinated chicks challenged with $10^6$ cfu per chick with *S. typhimurium,* 2 out of 9 birds died in the first 72 hours. For vaccinated chicks challenged with $10^8$ cfu, 4 out of 8 birds died in the first 72 hours following challenge. There was little difference between vaccination with $10^4$ or $10^6$ STM-1.

The results for both groups indicate that there is a significant level of protection being offered by the vaccination procedure when compared to the non-vaccinated group.

The challenge dose of $10^8$ cfu per chick administered subcutaneously was estimated at 100 times $LD_{50}$ for this Salmonella isolate and it is surprising that the challenge organism did not totally overwhelm the immune system of the in ovo vaccinated chick. In groups where a lower challenge dose of $10^6$ cfu per chick of the pathogenic Salmonella was used, there resulted a slower onset of the clinical effects. Based on these results, it is concluded that in ovo vaccination with STM-1 clearly protects chickens from subcutaneous challenge with virulent wild-type *Salmonella typhimurium.*

Microbiology data indicated that there was 100% colonization of STM-1 in chicks at day 4 post-hatch after vaccination in ovo with $10^4$ and $10^6$ STM-1. This organism was excreted in the faeces of vaccinated birds up to day 10, but by day 14, only 1 in 38 vaccinated birds were STM-1-positive in the intestine. Accordingly, STM-1 established systemic colonization of chicks after in ovo vaccinations.

EXAMPLE 9

Efficacy of in ovo Administration of *Salmonella typhimurium* STM-1 Against Subcutaneous Challenge by Virulent *Salmonella enteritidis*

The aim of this experiment is to determine if in ovo vaccination with STM-1 protects chicks from wild-type *S. enteritidis* challenged by subcutaneous administration.

Materials and Methods

The primary criterion for efficacy is mortality. The secondary measurements are differential fecal shedding and organ colonization. The vaccine was administered in ovo at $10^4$ or $10^6$ cfu per egg and challenge was given subcutaneously at $5\times10^7$ cfu per chick. Chicks received chemotherapy-free feed treated by gamma irradiation (Barastoc Stock Feeds, St Arnaud, Victoria) in 10 kg vacuum sealed multiwall paper and PVC containers. Each box was individually tested for the presence of Salmonella.

Hatched chickens were reared under infra-red heating lamps in accordance with general practices. Feed and water was available ad libitum throughout the trial period. The challenge strain was *S. enteritidis* strain 446302.

The eggs were vaccinated on the eighteenth day and incubation with $10^4$ or $10^6$ cfu per egg and chicks were challenged on the seventh day after hatch.

Results

The percentage hatchability of the eggs in the unvaccinated group, the $10^4$ cfu per egg vaccinated group and the $10^6$ cfu per egg vaccinated group were 87.2%, 95.6% and 69.6%, respectively. The respective body weights were 49.0 g, 48.3 g and 45.0 g. Hatchability was dependent on incubator performance and the low hatchability rate for the $10^6$ cfu per egg vaccination was probably due to the incubator rather than the vaccination.

In the non-vaccinated chicks challenged at $5\times10^7$ cfu per chick with wild-type *S. enteritidis,* there were rapid deaths (11 of 12 chicks by day 5). In the vaccinated chicks challenged with the same amount of *S. enteritidis,* there was a different pattern of chick deaths over an extended period of time. Eggs vaccinated with $10^6$ cfu per egg and then challenged resulted in 4 out of 8 birds dying in the first 6 days and one death after day 8. The eggs vaccinated with $10^4$ cfu per egg resulted in 4 deaths out of 11 birds on days 4 to 6 post-challenge and one death one at day 11 and one death at day 13. These results indicate that there is marked degree of cross-protection being offered by the vaccination procedure when compared to the non-vaccinated group.

The challenge dose of $5\times10^7$ cfu per chick administered subcutaneously was estimated at 100 times $LD_{50}$ for this Salmonella isolate.

Analysis of the serum IgG levels in the hatched chicks showed a higher average IgG level in vaccinated birds compared to non-vaccinated birds. This result shows that any in ovo vaccination is effective in stimulating an IgG response in chicks and the results obtained are at least as good as those seen in chicks that have survived a wild-type Salmonella challenge.

The study confirmed that inoculation of 18 day chick embryos with either $10^4$ or $10^6$ cfu of STM-1 resulted in effective colonization in 100% of vaccinates by the time of hatch. In ovo vaccination confirmed cross protection against challenge with *S. enteritidis* challenged with a dose of $5\times10^7$ cfu subcutaneously administered.

EXAMPLE 10

Efficacy of in ovo Administration of *Salmonella typhimurium* STM-1 Against Oral Challenge with Virulent *Salmonella enteritidis*

The purpose of this experiment was to establish whether chicks vaccinated in ovo at 17 days with *S. typhimurium* STM-1 have less colonization of tissues by *S. enteritidis* at 7 and 14 days post oral challenge with that organism.

Materials and Methods

The primary criteria for efficacy are measurements of differential fecal shedding and organ colonization. The vaccine was administered in ovo at $10^2$ or $10^4$ cfu per egg and the challenge was given orally at $1\times10^7$ cfu per chick or $6\times10^8$ cfu per chick.

Chicks received chemotherapy-free feed treated by gamma irradiation (Barastoc Stock Feeds, St Arnaud, Victoria) in 10 kg vacuum sealed multiwall paper and PVC containers. Each box was individually tested for the presence of Salmonella.

Hatched chicks were reared under infra red heating lamps in accordance with general practices. Feed and water was available ad libitum throughout the trial period. The challenge strain was *Salmonella enteritidis* 446302.

Results

The effects of the vaccine on hatchability and average body weight are shown in Table 6. No differences were evident in hatchability or body weight.

TABLE 6

| Group | Incubator | Treatment | % Hatch of Fertile Eggs | Average Body Weight |
|---|---|---|---|---|
| A | 1 | $10^2$ cfu/egg | 95 | 41.6 g |
| B | 2 | $10^4$ cfu/egg | 93 | 42.0 g |
| C | 3 | unvaccinated | 90 | 41.5 g |

Following challenge with the virulent organism (*Salmonella enteritidis*), only 1 chick died in the post-challenge period. This chick hatched from eggs vaccinated with $10^2$ cfu per egg. This is probably an accidental death rather than attributable to Salmonella infection.

With regard to weight gain, the chickens were uniform throughout the trial period. At day 4 post-hatch, 49 out of 50 chicks that were vaccinated with STM-1 in ovo shed the vaccine strain. The results are shown in Table 7.

TABLE 7

| Box # | Treatment | No. of Chicks | +ve STM-1 | Chall. Dose × $LD_{50}$ | +ve Group D (*S. enteritidis*) |
|---|---|---|---|---|---|
| 1 | Vacc $10^2$ cfu (day 4 post-hatch) | 13 | 13/13 | 1 | — |
| 2 | Vacc $10^2$ cfu (day 4 post-hatch) | 13 | 13/13 | 100 | — |
| 3 | Vacc $10^4$ cfu | 13 | 13/13 | 1 | — |
| 4 | " | 11 | 10/11 | 100 | — |
| 5 | Non vacc. | 12 | 1/12 | 1 | 9/12 |
| 6 | " | 11 | — | 100 | 9/11 |

— stands for non-detectable *S. enteriditis*

The results show that the vaccination procedure is safe, does not appear to affect the hatch rate or chick viability and is ideally suited for large numbers of broiler hatchings.

EXAMPLE 11

Determination of the Ability of the *Salmonella typhimurium* STM-1 Organism to Replicate In Ovo After Administration at 17 Days of Incubation The objective of this experiment was to assess the amount of recoverable *S. typhimurium* STM-1 organism from homogenized in ovo tissue over a 4 day incubation period (days 17–21 of incubation) after the administration of $10^2$ cfu per egg or $10^4$ cfu per egg of the STM-1 organism via the air sac.

Materials and Methods

The STM-1 organism was administered through the shell into the air sac space at day 17 of incubation. The primary measurement was estimation of the colony forming units of the STM-1 in egg shell tissue at a series of designated time intervals after incubation.

Seventeen day old incubated eggs were inoculated as follows:

18 eggs at $10^2$ cfu per egg;

18 eggs at $10^4$ cfu per egg.

Administration into the air sac was via a 26 gauge needle. At 2½, 26, 45, 69 and 100 hours post-vaccination, eggs were homogenized and cultured.

Homogenization occurred by a Waring blender. Aliquots of 100 ml of blending liquid comprising 50 ml of nutrient broth with 1% w/v yeast extract and 50 ml of PBS were added. The contents were homogenized for 60 seconds at low speed and retained for culture.

Results

No STM-1 colonies were present at any dilution when assayed at 2½ hours. At 26 hours post incubation in one egg (vaccinated at $10^4$ cfu per egg/egg), STM-1 was recorded in 100 $\mu$l and 1.0 ml plates (2 and 8 colonies, respectively giving an estimated egg count of $1.2\times10^3$ cfu). A dramatic increase in replication of STM-1 occurred after this time in all eggs tested. Results are shown in Table 8:

TABLE 8

| | egg count @ 69 hours | egg count @ 100 hours |
|---|---|---|
| Eggs vaccinated @ $10^2$ cfu of STM-1 | $7 \times 10^4$ | $1.2 \times 10^8$ |
| | $4 \times 10^5$ | $3 \times 10^7$ |
| | $9 \times 10^5$ | $1.5 \times 10^8$ |
| Eggs vaccinated @ $10^4$ cfu of STM-1 | $6 \times 10^5$ | $1.2 \times 10^8$ |
| | $9 \times 10^5$ | $1.2 \times 10^8$ |
| | $1 \times 10^5$ | $3 \times 10^6$ |

The results show that there is an initial stationary phase for the first at least 45 hours with no evidence of replication of STM-1 organism in ovo.

In the period 45 to 100 hours, there is significant replication of STM-1.

EXAMPLE 12

Determination of the Ability of *Salmonella typhimurium* STM-1 Organism to Replicate In Ovo After Administration into the Egg at 14 Days of Incubation The objective of this experiment was to assess the amount of recoverable STM-1 organisms from the eggs over a 7 day incubation period (14 to 21 days after administration of $10^2$ cfu per egg into the air sac).

Materials and Methods

The STM-1 organism was administered through the shell into the air sac. Primary measurement is an estimation of colony forming units STM-1 within egg shell tissue at a series of designated time intervals after incubation.

Fourteen day incubated eggs were inoculated as follows:

1. 36 eggs at $10^2$ cfu per egg 2. 9 eggs inoculated with 0.1 ml of PBS

Seventeen day incubated eggs were inoculated as follows:

1. 30 eggs at $10^2$ cfu per egg 2. 15 eggs at $10^1$ cfu per egg

Ten eggs not treated were retained as controls.

Bacterial replication was assessed at 24, 72, 96 and 168 hours after inoculation (with dosages indicated) by homogenizing eggs as in Example 11, and thereafter counting the number of organisms present. Two eggs were analyzed at each time point.

| Results | |
|---|---|
| Replication after 24 hours: | |
| 17 days @ $10^1$ | $9.0 \times 10^3$ cfu |
| 14 days @ $10^2$ | $4.5 \times 10^5$ cfu |
| | negative |
| 17 days @ $10^2$ | $7.7 \times 10^4$ cfu |
| | $2.1 \times 10^4$ cfu |
| Replication after 72 hours: | |
| 14 days @ $10^2$ | $1.8 \times 10^5$ cfu |
| | $1.6 \times 10^5$ cfu |
| 17 days @ $10^2$ | $1.3 \times 10^5$ cfu |
| | $0.2 \times 10^5$ cfu |
| Replication after 96 hours: | |
| 17 days @ $10^2$ | $<10^4$ cfu |
| | $8.0 \times 10^5$ cfu |
| 17 days @ $10^1$ | $9.0 \times 10^7$ cfu |
| | $8.0 \times 10^6$ cfu |
| Replication after 168 hours: | |
| 14 days @ $10^2$ | $4.0 \times 10^6$ cfu |
| | $2.0 \times 10^6$ |

The administered organisms were not embryotoxic. The above results show evidence of significant replication of STM-1 organisms in the eggs in the first 24 hours.

Eggs inoculated as early as 14 days after fertilization with $10^1$ cfu/egg of STM-1 contain $10^6$ organisms prior to hatching at day 21 (168 hours replication), indicating the STM-1 organism is capable of significant replication within the egg even when present at an initial low inoculum.

Embryo tissue as well as the air sac were analysed during the incubation period for bacterial growth. The STM-1 organism was not incorporated into organs/tissue whilst in ovo. Bacterial replication was shown to take place within the air sac. When chicks pierce the air sac membrane prior to hatching there is rapid replication of STM-1 within the developing chick. STM-1 was isolated in all organs tested at days 4 and 8 post-hatch, with the exception, of course, of the controls where no STM-1 was present either in eggs or chicks derived therefrom.

EXAMPLE 13

Viability of Developing Embryo Following in ovo Inoculation of Salmonella Organisms at Different Sites of the Egg The object of this experiment was to compare the viability of the developing chick embryo following in ovo inoculation of Salmonella organisms into the air sac, yolk sac and chorioalantoic membrane (CAM).

Materials and Methods

Inoculations were made into the air sac, yolk sac and CAM using $1\times10^6$ cfu of either STM-1, or virulent strains of *Salmonella typhimurium* or *Salmonella enteritidis*. Seventeen day incubated eggs were used in this experiment. Virulent Salmonella species used were *Salmonella typhimurium* 82/6915 and *Salmonella enteritidis* 446382.

| Results<br>The results of this experiment were as follows: | |
|---|---|
| Air Sac Inoculation | |
| STM-1 | 7 out of 7 hatched |
| *S. typhimurium* | 2 out of 4 hatched |
| *S. enteritidis* | 6 out of 8 hatched |
| Yolk Sac Inoculation | |
| STM-1 | 1 out of 7 hatched (1 egg was chipped which was viable at 20 days)<br>5 out of 7 died at 21 days |
| *S. typhimurium* | 7 out of 7 dead in 24 hours |
| *S. enteritidis* | 7 out of 7 dead in 24 hours |
| CAM Inoculation | |
| STM-1 | 2 out of 7 hatched<br>5 out of 7 dead at 21 days |
| *S. typhimurium* | 7 out of 7 dead in 24 hours |
| *S. enteritidis* | 7 out of 7 dead in 24 hours |

The results showed that the administration of the two known Salmonella pathogens, i.e., *Salmonella typhimurium* 82/6915 and *Salmonella enteritidis* 446302, via the yolk sac and CAM routes, results in rapid embryo death. These routes of administration mimic the parenteral route such as subcutaneous administration into a hatched chick.

The results also show that the two known pathogens did not exert an equivalent effect with the same dose of inoculation when administered via the air sac. In the case of *S. enteritidis,* there appeared to be no adverse affect on chick viability.

It is postulated that the organism resides and replicates within the air sac and that the chick is not infected until it breaks through the air sac membrane in the 24 hour period prior to hatching.

The results also show that *Salmonella typhimurium* STM-1 is of lower pathogenicity than the other two known pathogenic strains. While chick viability is compromised following STM-1 inoculation into the yolk sac and CAM, the effect of the inoculation was not as deleterious on the viability of the embryos compared to inoculation of the known pathogenic strains.

EXAMPLE 14

Expression of Antigenic Epitopes in *Salmonella typhimurium* STM-1

The present invention extends to a vaccine comprising Salmonella species of the type including *Salmonella typhimurium* STM-1 in order to immunize a chick against a virulent form of the same organism or an immunologically cross-reactive organism. The present invention also extends to the use of a Salmonella species carrying a recombinantly expressed antigen such as an antigen from another avian pathogenic species.

A number of vectors capable of expressing genetic sequences in Salmonella have been published and may be used in accordance with the present invention. Such vectors include those described by Schodel et al., *Vaccine,* 11: 143–148, 1993, and Schodel et al., *J. Immunol.,* 12: 4317–4321, 1990. Alternatively, techniques such as transduction, conjugation and/or transformation may be used to generate strains of Salmonella expressing antigens not normally associated with that particular strain. Such modified Salmonella strains are useful as multivalent vaccines.

Once a genetically modified *Salmonella typhimurium* STM-1 strain is produced, it is administered to the air sac according to the methods herein described. Generally, inoculation is made at day 17 or 18 of the incubation period. After hatching, recipient chickens are challenged with the causative agent for which the antigenic determinant is isolated and/or serological analysis is conducted and/or microbiological analysis is conducted. Such vaccinated chickens should exhibit similar protection rates against virulent forms of the source of the antigenic epitopes as occur when STM-1 alone is used to vaccinate eggs.

EXAMPLE 15

Production of Aro Mutants

Aro deletion mutants are prepared according to the methods as described in U.S. Pat. Nos. 4,735,801, 5,210,035 and 4,837,151, all of which are incorporated herein by reference in their entirety. Wild-type Salmonella, Shigella, Klebsiella, Enterobacter, Serratia, Proteus, Yersinia, Vibrio, Aewromanas, Pasteurella, Pseudomonas, Acinetobacter, Moraxella, Flavobacterium and *Escherichia coli* are subjected to phage transduction using phage carrying a Tn 10 transposon inserted into the aroA, aroB, aroC or aroD. Resultant mutants are selected for tetracycline resistance.

Genetically modified organisms, such as Salmonella strains, are administered to the air sac according to the methods herein described. After hatching, recipient chickens are challenged with wild-type strains. Vaccinated chickens exhibit protection against virulent wild-type strains.

What is claimed is:

1. A method for immunizing an avian species against infection by a pathogenic Salmonella microorganism, said method comprising administering in ovo to an air sac of an egg an attenuated Salmonella microorganism which:

(a) exhibits auxotrophy to one or more growth factors selected from the group consisting of phenylalanine, tyrosine, tryptophan and para-aminobenzoic acid such that it is incapable of growing on a minimal medium in the absence of said one or more growth factors; and (b) is capable of colonizing one or more tissues in an embryo prior to hatching in an amount and under conditions effective to induce an immune response in the embryo before or immediately after hatching against a virulent form of said attenuated Salmonella microorganism or a microorganism expressing an immunologically cross-reactive antigen.

2. A method according to claim 1 wherein the avian species is selected from the group consisting of chickens, ducks, turkeys, geese, bantams, quail and pigeons.

3. A method according to claim 2 wherein the avian species is chickens.

4. A method according to claim 1 wherein the attenuated Salmonella microorganism is a Salmonella selected from the group consisting of *Salmonella typhimurium, Salmonella paratyphi* A or C, *Salmonella schottmulleri, Salmonella choleraesuis, Salmonella montevideo, Salmonella newport, Salmonella enteritidis, Salmonella gallinarum, Salmonella pullorum, Salmonella abortusovi, Salmonella abortus-equi, Salmonella dublin, Salmonella sofia, Salmonella havana, Salmonella bovismorbificians, Salmonella hadar, Salmonella arizonae* and *Salmonella anatum.*

5. A method according to claim 4 wherein the attenuated Salmonella microorganism is *Salmonella typhimurium.*

6. A method according to claim 5 wherein the attenuated Salmonella microorganism is *Salmonella typhimurium* strain STM-1, deposited at the Australian Government Analytical Laboratories under Accession number N93/43266.

7. A method according to claim 1 wherein the attenuated Salmonella microorganism is incapable of synthesizing chorismate such that the Salmonella microorganism is incapable of growing on minimal medium.

8. A method according to claim 7 wherein the attenuated Salmonella microorganism carries a nucleotide substitution, deletion, insertion, or combination thereof in one or more genes selected from the group consisting of aroA, aroB, aroC and aroD.

9. A method according to claim 8 wherein the attenuated Salmonella microorganism carries a deletion in at least one gene selected from the group consisting of aroA, aroB, aroC and aroD.

10. A method according to claim 1 wherein the attenuated Salmonella microorganism breaks through the air sac and the embryo is exposed to the vaccine.

11. A method according to claim 1 wherein the attenuated Salmonella microorganism competitively excludes pathogenic microorganisms from a newly-hatched bird.

12. Salmonella typhimurium STM-1 deposited at the Australian Government Analytical Laboratories under Accession number N93/43266.

13. A fertilized egg from an avian species having an air sac wherein the air sac is inoculated with an attenuated Salmonella microorganism which:

(a) exhibits auxotrophy to one or more growth factors selected from the group consisting of phenylalanine, tyrosine, tryptophan and para-aminobenzoic acid such that it is incapable of growing on a minimal medium in the absence of said one or more growth factors;

(b) is capable of colonizing one or more tissues in an embryo prior to hatching; and (c) is capable of inducing before or immediately after hatching an immune response in the embryo against a virulent form of said Salmonella microorganism or a microorganism expressing an immunologically cross-reactive antigen.

14. A fertilized egg according to claim 13 wherein in the avian species is selected from the group consisting of chickens, ducks, turkeys, geese, bantams, quail and pigeons.

15. A fertilized egg according to claim 14 wherein the avian species is chickens.

16. A fertilized egg according to claim 13 wherein the attenuated Salmonella microorganism is a Salmonella selected from the group consisting of *Salmonella typhimurium, Salmonella paratyphi* A or C, *Salmonella schottmulleri, Salmonella choleraesuis, Salmonella montevideo, Salmonella newport, Salmonella enteritidis, Salmonella gallinarum, Salmonella pullorum, Salmonella abortusovi, Salmonella abortus-equi, Salmonella dublin, Salmonella sofia, Salmonella havana, Salmonella bovismorbificians, Salmonella hadar, Salmonella arizonae* and *Salmonella anatum.*

17. A fertilized egg according to claim 16 wherein the attenuated Salmonella microorganism is *Salmonella typhimurium* or *Salmonella enteritidis.*

18. A fertilized egg according to claim 17 wherein the attenuated Salmonella microorganism is *Salmonella typhimurium* strain STM-1, deposited at the Australian Government Analytical Laboratories under Accession number N93/43266.

19. A fertilized egg according to claim 13 wherein the attenuated Salmonella microorganism is incapable of synthesizing chorismate such that the microorganism is incapable of growing on minimal medium.

20. A fertilized egg according to claim 19 wherein the attenuated Salmonella microorganism carries a nucleotide substitution, deletion, insertion, or combination thereof in one or more genes selected from the group consisting of aroA, aroB, aroC and aroD.

21. A fertilized egg according to claim 20 wherein the attenuated Salmonella microorganism carries a deletion in at least one gene selected from the group consisting of aroA, aroB, aroC and aroD.

22. A fertilized egg according to claim 21 wherein the attenuated Salmonella microorganism carries a deletion in aroA.

23. A fertilized egg according to claim 20 wherein the attenuated Salmonella microorganism further carries a mutation in a gene encoding an enzyme of a biosynthetic pathway other than an Aro pathway.

24. A fertilized egg according to claim 23 wherein the biosynthetic pathway is the biosynthesis of serine.

25. A fertilized egg according to claim 13 wherein the embryo is exposed to the vaccine after breaking through the air sac.

26. A fertilized egg according to claim 13 wherein the attenuated Salmonella microorganism competitively excludes pathogenic microorganisms from a newly-hatched bird.

* * * * *